United States Patent
Womack et al.

(10) Patent No.: US 12,252,465 B2
(45) Date of Patent: Mar. 18, 2025

(54) ENOL ETHER PROPERFUME

(71) Applicant: FIRMENICH SA, Satigny (CH)

(72) Inventors: Gary Bernard Womack, Plainsboro, NJ (US); Brinda Indradas, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 234 days.

(21) Appl. No.: 17/754,486

(22) PCT Filed: Dec. 1, 2020

(86) PCT No.: PCT/EP2020/084133
§ 371 (c)(1),
(2) Date: Apr. 4, 2022

(87) PCT Pub. No.: WO2021/110680
PCT Pub. Date: Jun. 10, 2021

(65) Prior Publication Data
US 2024/0059640 A1    Feb. 22, 2024

Related U.S. Application Data

(60) Provisional application No. 62/942,970, filed on Dec. 3, 2019.

(30) Foreign Application Priority Data

Jan. 9, 2020  (EP) .................................... 20150871

(51) Int. Cl.
| | |
|---|---|
| *C07C 43/166* | (2006.01) |
| *A61K 8/33* | (2006.01) |
| *A61Q 13/00* | (2006.01) |
| *C11D 3/50* | (2006.01) |

(52) U.S. Cl.
CPC ............ *C07C 43/166* (2013.01); *A61K 8/33* (2013.01); *A61Q 13/00* (2013.01); *C11D 3/50* (2013.01)

(58) Field of Classification Search
CPC ....... C07C 43/166; C07C 43/23; C07C 45/34; C07C 45/32; C07C 67/39; C07C 41/26; C07C 49/78; C07C 49/04; C07C 69/78; A61K 8/33; A61K 2800/57; C11D 3/50; C11B 9/00; A61Q 13/00; A61Q 5/12; A61Q 15/00
USPC .......................................................... 512/1
See application file for complete search history.

(56) References Cited

U.S. PATENT DOCUMENTS 5,084,490 A * 1/1992 McArdle ............... C07C 43/215
568/657

FOREIGN PATENT DOCUMENTS

WO    2012085287 A1    1/1962

OTHER PUBLICATIONS

Saumya Dabral et al, "Mechanistic studies of base-catalysed lignin depolymerisation in dimethyl carbonate", Green Chemistry, vol. 20, No. 1, Nov. 24, 2017 (Nov. 24, 2017), pp. 170-182.
Wittig et al, "Phosphinealkylenes as olefination reagents. VI", Chemische Berichte, VCH, DE, vol. 95, Jan. 1, 1962 (Jan. 1, 1962), pp. 2514-2525.
International Search Report and Written Opinion for corresponding PCT/EP2020/084133 mailed Feb. 18, 2021; 10 pages.

* cited by examiner

*Primary Examiner* — Jessica Whiteley
(74) *Attorney, Agent, or Firm* — Armstrong Teasdale LLP

(57) ABSTRACT

Described herein are compounds of formula (I) as properfume compounds, as well as a method to release a compound being a carbonyl of formula (II), a formate ester of formula (III) and/or an alcohol of formula (IV), by exposing the compound of formula (I) to an environment wherein it is oxidized. Also described herein are a perfuming composition and a perfume consumer product including at least one compound of formula (I).

15 Claims, No Drawings

ENOL ETHER PROPERFUME

CROSS-REFERENCE TO RELATED APPLICATIONS

This application is a U.S. National Phase Application of International Patent Application No. PCT/EP2020/084133, filed Dec. 1, 2020, which claims priority to European Patent Application No. 20150871.0, filed Jan. 9, 2020, and to U.S. Provisional Patent Application No. 62/942,970, filed Dec. 3, 2019, each of which is hereby incorporated by reference herein in its entirety.

TECHNICAL FIELD

The present invention relates to compounds of formula (I) as properfume compounds. In particular, the present invention relates to a method to release a compound being a carbonyl of formula (II), a formate ester of formula (III) and/or an alcohol of formula (IV), by exposing the compound of formula (I) to an environment wherein it is oxidized. Moreover, the present invention relates to a perfuming composition and a perfume consumer product comprising at least one compound of formula (I).

BACKGROUND

The perfume industry has a particular interest for compositions or additives which are capable of prolonging or enhancing the perfuming effect of at least one perfuming ingredient a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients are unstable and need to be protected against slow degradation prior to their use. Long-lasting perfumes are desirable for various applications, as for example fine or functional perfumery or cosmetic preparations. The washing and softening of textiles is a particular field in which there is a constant need to enable the effect of active substances, in particular perfumes, or perfuming compositions, to be effective for a certain period of time after washing, softening and drying. Indeed, many active substances which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

It has now been surprisingly found that enol ether compounds according to the present invention solve the above-mentioned problems and are capable of efficiently releasing a compound being a carbonyl of formula (II), a formate ester of formula (III) and/or an alcohol of formula (IV).

DETAILED DESCRIPTION

Olfaction is a complex and dynamic process, and controlling the release profile of volatile fragrance compounds may maximize the impact of fragrance formulations and enrich the sensorial experience. Profragrances, such as the compounds of the present invention add a dimension of control and long-lastingness to the release profile of highly volatile perfumery raw materials (PRMs).

Without intending to be limited to any particular theory, the compounds of the present invention may achieve their effect on the olfactive properties of a perfuming composition by tethering the PRM to a molecular anchor and requiring a specific reaction mechanism under certain environmental conditions to release the volatile PRM from this anchor. In the present invention, the release of one, two or up to three PRMs is prompted by oxidation when the profragrance is exposed to the oxygen in ambient air.

The first object of the present invention is a method to release from a precursor compound, compounds selected from the group consisting of
a) a carbonyl compound of formula

wherein when $R^2$ represents a $OR^{2'}$ wherein $R^{2'}$ represents a $C_{1-12}$ alkyl group, a $C_{3-12}$ alkenyl group, a phenethyl group or a benzyl group, then $R^1$ is a phenyl group optionally substituted by one or two $R^{1'}$ group wherein $R^{1'}$, simultaneously or independently, represents a hydroxyl group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring;

when $R^2$ represents a $C_{1-6}$ alkyl or a $C_{6-10}$ aryl group each optionally substituted by a hydroxyl group, a $C_{1-3}$ alkyl group, a $C_{1-3}$ alkoxy group, then $R^1$ represents a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula

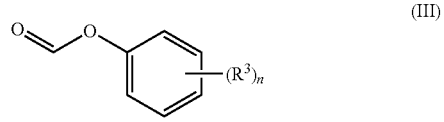

wherein n represent an integer between 1 and 5;
$R^3$, simultaneously or independently, represents at least one substituent of the aromatic ring and is a $C_{1-6}$ alkyl group optionally substituted by a hydroxy, $C_{1-6}$ alkoxy or oxo group; a $C_{4-7}$ oxacycloalkyl or oxacycloalkenyl group optionally substituted with a $C_{1-3}$ alkyl or a methylene group; a $C_{2-6}$ alkenyl group; a $C_{1-6}$ alkoxy group; or a $R^bOCO$ group wherein $R^b$ is a hydrogen atom, a $C_{1-7}$ alkyl group, a $C_{2-7}$ alkenyl group, a $C_{3-7}$ cycloalkyl group, a benzyl group or a phenethyl group;

c) an alcohol of formula

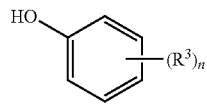

(IV)

wherein $R^3$ has the same meaning as defined above;
wherein at least one of the compounds of formula (II), (III) or (IV) is an active compound;
wherein the precursor compound comprises a compound of formula (I)

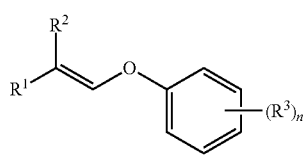

(I)

in the form of any one of its stereoisomers or a mixture thereof and wherein n, $R^1$, $R^2$ and $R^3$ have the same meaning as defined above; by exposing the precursor compound of formula (I) to an environment wherein the compound is oxidized; i.e. ambient conditions.

The terms "active compound", "active volatile compound", "active volatile carbonyl, formate ester and/or alcohol" or the similar, are understood as carbonyl, formate ester and/or alcohol compounds being capable of bringing a benefit or effect into its surrounding environment. In particular the "active compound" is selected from the group consisting of a perfuming ingredient, flavoring ingredient, malodor counteracting ingredient, antimicrobial ingredient and insect repellent or attractant ingredient. Therefore, to be considered as an "active compound" the compound has to possess at least one property which renders it useful as a perfuming ingredient, as a malodor counteracting ingredient, a flavoring ingredient, an antimicrobial ingredient and/ or as an insect repellent or attractant.

The term "perfuming ingredient" is understood as a compound which is used, for the primary purpose, as an active ingredient in perfuming preparations or compositions in order to impart a hedonic effect. In other words, a compound to be considered as being a perfuming ingredient, must be recognized by a skilled person in the art of perfumery as being able to impart or modify in a positive or pleasant way the odor of a composition, and not just as having an odor. The perfuming ingredient may impart an additional benefit beyond that of modifying or imparting an odor, such as long-lasting, blooming, malodour counteraction, antimicrobial effect, antiviral effect, microbial stability, pest control. The term "flavoring ingredient" is understood to as being capable of imparting a taste sensation to the taster's pallet. The term "malodor counteracting ingredient" is understood as being capable of reducing the perception of malodor, i.e. of an odor that is unpleasant or offensive to the human nose. The term "antimicrobial ingredient" is understood as being capable of killing microorganism or reducing or preventing their growth and/or accumulation and include antibacterial, antibiotic, antifungal, antiviral and antiparasitic ingredients. The term "insect attractant or repellent" is understood as a compound having a positive or negative effect on insects. Examples of insect attractant or repellent ingredients can be found in reference texts or in other works of a similar nature as for example: A. M. El-Sayed, The Pherobase 2005, http://www.pherobase.net.

According to the above and below mentioned embodiments of the invention, the method according to the present invention is particularly useful when the active compound is a perfuming ingredient, i.e. a perfuming carbonyl compound, formate ester and/or alcohol. A "perfuming carbonyl compound, formate ester and/or alcohol" is a compound, which is of use in the perfumery industry, i.e. a compound which is used as active ingredient in perfuming preparations or compositions in order to impart a hedonic effect. In other words, such a carbonyl compound, formate ester and/or alcohol, to be considered as being a perfuming one, must be recognized by a person skilled in the art of perfumery as being able to impart or modify in a positive or pleasant way the odor of a composition, and not just as having an odor. The perfuming carbonyl compound, formate ester and/or alcohol can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery.

Herein described, the terms "perfuming carbonyl compound, formate ester and/or alcohol" are also referred to as "perfuming compounds".

Practically, the invention is carried out exactly in the same manner, independently of the exact properties of the active carbonyl compound, formate ester or alcohol. Therefore, it is understood that, even if the invention will be further illustrated herein below with a specific reference to "perfuming compounds", the below embodiments are also applicable to other active carbonyl compound, formate ester and/or alcohol (i.e. it is possible to replace the expression "perfuming" with "flavoring", "malodor counteracting", "antibacterial", "antimicrobial," "insect attractant" or with "insect repellent" for instance).

The term "optionally" is understood that a certain group to be optionally substituted can or cannot be substituted with a certain functional group. The term "one or more" is understood as being substituted with 1 to 7, preferably 1 to 5 and more preferably 1 to 3 of a certain functional group.

The terms "alkyl" and "alkenyl" are understood as comprising branched and linear alkyl and alkenyl groups. The terms "alkenyl", "cycloalkenyl" and "heterocycloalkenyl" is understood as comprising 1, 2 or 3 olefinic double bonds, preferably 1 or 2 olefinic double bonds. The terms "cycloalkyl", "cycloalkenyl", "heterocycloalkyl" and "heterocycloalkenyl" are understood as comprising a monocyclic or fused, spiro and/or bridged bicyclic or tricyclic cycloalkyl, cycloalkenyl, heterocycloalkyl and heterocycloalkenyl groups, preferably monocyclic cycloalkyl, cycloalkenyl, heterocycloalkyl and heterocycloalkenyl groups.

The term "carbonyl" designates an ester or a ketone depending on the meaning of the $R^2$ group; i.e. the carbonyl compound of formula (II) is an ester when $R^2$ represents a $OR^{2'}$ or a ketone when $R^2$ represents a $C_{1-6}$ alkyl or a $C_{6-10}$ aryl group optionally substituted by a hydroxyl group, a $C_{1-3}$ alkyl group, a $C_{1-3}$ alkoxy group.

The term "aryl" are understood as comprising any group comprising at least one aromatic group such as phenyl, indenyl, indanyl, tetrahydronaphthalenyl or naphthalenyl group.

The term "oxo group" are understood as comprising any group of formula =O; i.e. such as a ketone or an aldehyde. In other words, a $C_{1-6}$ alkyl group optionally substituted an oxo group is an alkyl group having from 1 to 6 carbons and one of these carbon atoms, even the terminal carbon, may be substituted by a =O group instead of two hydrogen atoms.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters and each of said stereocenter can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore, the compound of formula (I) can be one stereoisomer or in the form of a composition of matter comprising, or consisting of, various stereoisomers.

According to any one of the above embodiments of the invention, said compound of formula (I) can be in the form of its E or Z isomer or of a mixture thereof, e.g. the invention comprises compositions of matter consisting of one or more compounds of formula (I), having the same chemical structure but differing by the configuration of the double bond.

According to a particular embodiment, when $R^2$ does not represent a $OR^{2'}$, compound (I) can be in the form of a mixture consisting of isomers E and Z and wherein said isomers E represent at least 50% of the total mixture, or even at least 60%, or even at least 70%, or even at least 75% (i.e a mixture E/Z comprised between 75/25 and 100/0). According to another particular embodiment, when $R^2$ represents a $OR^{2'}$, compound (I) can be in the form of a mixture consisting of isomers E and Z and wherein said isomers Z represent at least 50% of the total mixture, or even at least 60%, or even at least 70%, or even at least 75% (i.e a mixture Z/E comprised between 75/25 and 100/0).

According to any one of the embodiments of the invention, when $R^1$ may be a $C_{3-15}$ alkenyl, it is understood that the double bond is not adjacent to the carbon connecting $R^1$. In other words, compounds of formula (II) are not a conjugated enone and compounds of formula (I) are not a conjugated dienol ether.

According to any one of the embodiments of the invention, the compound of formula (I) is as defined above provided that when $R^1$ is methyl then $R^2$ is not methyl,
when $R^1$ is ethyl then $R^2$ is not ethyl,
1,3-dimethoxy-2-((2-phenylprop-1-en-1-yl)oxy)benzene, 1-methyl-4-((-2-methyl-4-(2,6,6-trimethylcyclohex-1-en-1-yl)buta-1,3-dien-1-yl)oxy)benzene, 1-methyl-4-((-2-methyl-4-(2,6,6-trimethylcyclohex-2-en-1-yl)buta-1,3-dien-1-yl)oxy)benzene and 1,2-dimethoxy-4-(1-(2-methoxyphenoxy)prop-1-en-2-yl)benzene are excluded.

According to any one of the embodiments of the invention, n may be 1, 2 or 3. Even more particularly, n may be 1 or 2.

According to a particular embodiment of the invention, $R^2$ may represents a $C_{1-6}$ alkyl or a phenyl group each optionally substituted a hydroxyl group, a $C_{1-3}$ alkyl group, a $C_{1-3}$ alkoxy group, then $R^1$ may represent a $C_{1-15}$ alkyl, $C_{3-15}$ alkenyl, $C_{6-10}$ aryl, $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group. $R^2$ may represent a phenyl group or a $C_{1-6}$ alkyl group optionally substituted by a hydroxyl group, a $C_{1-3}$ alkyl group, a $C_{1-3}$ alkoxy group, then $R^1$ may represent a $C_{1-12}$ alkyl, $C_{3-12}$ alkenyl, $C_{6-10}$ aryl, $C_{3-15}$ cycloalkyl or $C_{5-15}$ cycloalkenyl group, each optionally substituted with one or more of a $C_{1-8}$ alkyl, $C_{1-8}$ alkoxy, $C_{3-12}$ cycloalkyl, $C_{5-12}$ cycloalkenyl, carboxylic acid, $C_{1-4}$ carboxylic ester, $C_{6-10}$ aryl and/or $C_{6-10}$ aryloxy group. $R^2$ may represent a $C_{1-3}$ alkyl group and then $R^1$ may represent a $C_{6-10}$ aryl or $C_{1-10}$ alkyl group optionally substituted with a phenyl, a $C_{5-7}$ cycloalkyl and/or $C_{5-7}$ cycloalkenyl group, each optionally substituted with one or more of a $C_{1-4}$ alkyl and/or $C_{1-4}$ alkoxy group. $R^2$ may represent a $C_{1-3}$ alkyl group and then $R^1$ may represent a phenyl or $C_{1-10}$ alkyl group.

According to a particular embodiments of the invention, $R^2$ may represent a $OR^{2'}$ wherein $R^{2'}$ may represent a $C_{1-12}$ alkyl group, a $C_{3-12}$ alkenyl group, phenethyl group or a benzyl group, then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group; or two adjacent $R^{1'}$, when taken together, may represent a —O—$(CH_2)_m$—O— wherein m may be 1 or 2. $R^2$ may represent a $OR^{2'}$ wherein $R^{2'}$ may represent a $C_{1-8}$ alkyl group, a $C_{3-8}$ alkenyl group, phenethyl group or a benzyl group, then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group; or two adjacent $R^{1'}$, when taken together, may represent a —O—$(CH_2)_m$—O— wherein m may be 1 or 2. $R^2$ may represent a $OR^{2'}$ wherein $R^{2'}$ may represent a $C_{1-6}$ alkyl group, a $C_{3-6}$ alkenyl group, phenethyl group or a benzyl group, then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group; or two adjacent $R^{1'}$, when taken together, may represent a —O—$(CH_2)_m$—O— wherein m may be 1 or 2. $R^2$ may represent a $OR^{2'}$ wherein $R^{2'}$ may represent a $C_{1-6}$ alkyl group, a $C_{3-6}$ alkenyl group or a benzyl group, then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group. $R_2$ may represent a $OR^{2'}$ wherein $R^{2'}$ may represent a $C_{1-6}$ alkyl group or a benzyl group and then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group. $R_2$ may represent a $OR^{2'}$ wherein $R^{2'}$ may represent a $C_{1-4}$ alkyl group or a benzyl group and then $R^1$ may be a phenyl group optionally substituted by one or two $R^{1'}$ group wherein $R^{1'}$, simultaneously or independently, may represent a hydroxyl group, a $C_{1-3}$ alkyl group, a $C_{1-3}$ alkoxy group. $R^2$ may represent a $OR^{2'}$ wherein $R^{2'}$ may represent a $C_{1-4}$ alkyl group and then $R^1$ may be a phenyl group optionally substituted by one $R^{1'}$ group wherein $R^{1'}$ may represent a hydroxyl group, a methyl group, a methoxy group.

According to a particular embodiment of the invention, $R^1$ and $R^2$, when taken together, may form a $C_{5-16}$ cycloalkyl or $C_{5-16}$ cycloalkenyl group, each optionally substituted with one or more of a $C_{1-8}$ alkyl, $C_{1-8}$ alkoxy, $C_{3-8}$ cycloalkyl, $C_{5-8}$ cycloalkenyl and/or phenyl group. $R^1$ and $R^2$, when taken together, may form a $C_{5-8}$ cycloalkyl or $C_{5-8}$ cycloalkenyl group, each optionally substituted with one or more of a $C_{1-6}$ alkyl and/or $C_{1-3}$ alkoxy group. $R^1$ and $R^2$, when taken together, may form a $C_{5-6}$ cycloalkyl group optionally substituted with one, two or three of a $C_{1-5}$ alkyl group.

According to any one of the embodiments of the invention, $R^3$, simultaneously or independently, represents at least one substituent of the aromatic ring and is a $C_{1-6}$ alkyl group optionally substituted by a $C_{1-6}$ alkoxy or an oxo group; a $C_{4-7}$ oxacycloalkyl or oxacycloalkenyl group optionally substituted with a $C_{1-3}$ alkyl or a methylene group; a $C_{2-6}$ alkenyl group; a $C_{1-6}$ alkoxy group; or a $R^bOCO$ group wherein $R^b$ is a hydrogen atom, a $C_{1-7}$ alkyl group, a $C_{2-7}$ alkenyl group, a benzyl group or a phenethyl group.

According to any one of the embodiments of the invention, $R^3$, simultaneously or independently, may represent at least one substituent of the aromatic ring and is a $C_{1-6}$ alkyl group optionally substituted by a hydroxy, $C_{1-3}$ alkoxy or oxo group; a $C_{4-7}$ oxacycloalkyl or oxacycloalkenyl group optionally substituted with a methyl or a methylene group; a $C_{2-6}$ alkenyl group; a $C_{1-6}$ alkoxy group; or a $R^bOCO$ group wherein $R^b$ may be a hydrogen atom, a $C_{1-7}$ alkyl group, a $C_{2-7}$ alkenyl group, a $C_{5-7}$ cycloalkyl group, a benzyl group or a phenethyl group. $R^3$, simultaneously or independently, may represent a $C_{1-6}$ alkyl group optionally substituted by a hydroxy, a $C_{1-2}$ alkoxy or an oxo group; a $C_{2-6}$ alkenyl group; a $C_{1-3}$ alkoxy group; or a $R^bOCO$ group wherein $R^b$ may be a hydrogen atom, a $C_{1-7}$ alkyl, a $C_{2-7}$ alkenyl or a cyclohexyl group. $R^3$, simultaneously or independently, may represent a $C_{1-4}$ alkyl group optionally substituted by a hydroxy, a methoxy or an oxo group; a $C_{2-3}$ alkenyl group; or a $C_{1-2}$ alkoxy. $R^3$, simultaneously or independently, may represent a methoxy group, a ethoxy group, hydroxymethyl group, a methoxymethyl group, a methyl group, a methoxycarbonyl group, a (hex-3-en-1-yloxy)carbonyl group, a propyl group, a propen-1-yl group, a formyl group, a propen-2-yl group or a 3-oxobutyl group. $R^3$, simultaneously or independently, may represent a methoxy group, a propyl group, a propen-1-yl group, a formyl group, a propen-2-yl group or a 3-oxobutyl group.

According to a particular embodiment, at least two of the compounds of formula (II), (III) and (IV) are active compounds. Even more, the compounds of formula (II), (III) and (IV) are active compounds.

According to a particular embodiment, the carbonyl compound of formula (II), the formate ester of formula (III) and/or the active alcohol of formula (IV) are perfuming ingredients. For a person skilled in the art it is also evident that compounds of formula (II), (III) and (IV) according to the present invention are inherently volatile compounds.

The carbonyl compound, formate ester and/or alcohol may be advantageously characterized by a vapor pressure above 1.0 Pa, as obtained by calculation using the software EPIwin v. 3.10 (2000, available at the US Environmental Protection Agency). According to another embodiment, the vapor pressure of the ketone, formate ester and/or alcohol may be above 5.0, or even above 7.0 Pa.

According to a particular embodiment, the compound of formula (I) is non-volatile. The compound of formula (I) may be advantageously characterized by a vapor pressure below 0.01 Pa, as obtained by calculation using the software EPIwin v. 3.10 (2000, available at the US Environmental Protection Agency). According to a preferred embodiment, the vapor pressure is below 0.001 Pa.

According to a particular embodiment, the carbonyl compound of formula (II) is a ketone selected from the group consisting of acetophenone, p-methylacetophenone, p-methoxyacetophenone, benzophenone, 1-(5,6,7,8-tetrahydronaphthalen-2-yl)ethan-1-one, 1-(naphthalen-2-yl)ethan-1-one, 1-(naphthalen-1-yl)ethan-1-one, 1-(p-tolyl)propan-1-one, 1-(1,1,2,3,3,6-hexamethyl-2,3-dihydro-1H-inden-5-yl)ethan-1-one, 1-(3,5,5,6,8,8-hexamethyl-5,6,7,8-tetrahydronaphthalen-2-yl)ethan-1-one, 1-(3-isopropyl-1,1,2,6-tetramethyl-2,3-dihydro-1H-inden-5-yl)ethan-1-one, 1-(6-(tert-butyl)-1,1-dimethyl-2,3-dihydro-1H-inden-4-yl)ethan-1-one, acetone, 3-hexanone, 4-nonanone, 5-undecanone, cyclohexanone, cyclopentanone, cyclooctanone, cycloheptanone, cyclododecanone, cyclodecanone, 2-butanone, 2-pentanone, 2-hexanone, 2-heptanone, 2-octanone, 2-nonanone, 2-decanone, 2-undecanone, 2-tridecanone, 2-pentadecanone, 3-heptanone, 3-octanone, 5-methyl-3-heptanone, 6-methyl-5-hepten-2-one, 2,6-dimethyl-7-octen-4-one, 2-(sec-butyl)cyclohexan-1-one, 2-(tert-butyl)cyclohexan-1-one, 4-(tert-butyl)cyclohexan-1-one, 4-(tert-pentyl)cyclohexan-1-one, 5-isopropyl-2-methylcyclohexan-1-one, 2-isopropyl-5-methylcyclohexan-1-one, 2,2,6-trimethylcyclohexan-1-one, 2,2,4-trimethylbicyclo[3.1.1]heptan-3-one, thujanone, 2-ethyl-4,4-dimethylcyclohexan-1-one, 1,7,7-trimethylbicyclo[2.2.1]heptan-2-one, plicatone, thujopsan-4-one, 1,3,3-trimethylbicyclo[2.2.1]heptan-2-one, 4-phenyl-2-butanone, 4-(4-methoxyphenyl)-2-butanone, zingerone, 4-(1,3-benzodioxol-5-yl)-2-butanone, 2-cyclohexyl-4-methyl-2-pentanone, 1-(4-methyl-1-phenoxy)-2-propanone, 4-(2,6,6-trimethylcyclohex-2-en-1-yl)butan-2-one, 4-(2,6,6-trimethylcyclohex-1-en-1-yl)butan-2-one, (5-E/Z)-6,10-dimethylundeca-5,9-dien-2-one, cyclopentadecanone, (Z)-cycloheptadec-9-en-1-one, 3-methylcyclopentadecan-1-one, 3-methyl-5-cyclopentadecen-1-one, (Z)-cyclopentadec-4-en-1-one, 4,8-cyclododecadien-1-one, 7-methyl-2H-benzo[b][1,4]dioxepin-3(4H)-one, 7-propyl-2H-benzo[b][1,4]dioxepin-3(4H)-one, 1-(5-propylbenzo[d][1,3]dioxol-2-yl)ethan-1-one, 4,4a,6,7,8,8a-hexahydro-1,4-methanonaphthalen-5(1H)-one, 2-pentylcyclopentan-1-one, 2-heptylcyclopentan-1-one, 2-(hex-5-en-1-yl)cyclopentan-1-one, 2,2,5-trimethyl-5-pentylcyclopentan-1-one, Iso-E-Super, 1-(5-isopropyl-2-methylcyclohex-2-en-1-yl)propan-1-one, 2,2,7,9-tetramethylspiro[5.5]undec-7-en-1-one, 4-ethyl-8-methyloctahydronaphthalen-1(2H)-one, 1-(3,3-dimethylcyclohexyl)ethan-1-one, 2,6,6-trimethylcycloheptan-1-one and 3,6,8,8-tetramethylhexahydro-1H-3a,7-methanoazulen-5(4H)-one.

Particularly, the carbonyl compound of formula (II) is a ketone selected from the group consisting of acetophenone, 2-undecanone, 3-heptanone, 2-ethyl-4,4-dimethylcyclohexan-1-one, 2-pentylcyclopentan-1-one, and 4-(tert-pentyl)cyclohexan-1-one.

According to a particular embodiment, the carbonyl compound of formula (II) is an ester selected from the group consisting of methyl benzoate, ethyl benzoate, propyl benzoate, butyl benzoate, pentyl benzoate, hexyl benzoate, heptyl benzoate, (Z)-hex-3-en-1-yl benzoate, isopropyl benzoate, isobutyl benzoate, sec-butyl benzoate, isoamyl benzoate, sec-pentyl benzoate, benzyl benzoate, octyl benzoate, 2-phenylethyl benzoate, $C_{1-4}$ alkyl 4-methoxybenzoates, $C_{1-4}$ alkyl 4-methylbenzoates, $C_{1-4}$ alkyl 2-methoxybenzoates, $C_{1-4}$ alkyl 2-methyl benzoates and $C_{1-4}$ alkyl benzo[d][1,3]dioxole-5-carboxylate.

Particularly, the carbonyl compound of formula (II) is an ester selected from the group consisting of methyl benzoate, ethyl benzoate, butyl benzoate, hexyl benzoate, octyl benzoate, (Z)-hex-3-en-1-yl benzoate, 2-phenylethyl benzoate, methyl 4-methylbenzoate and methyl 4-methoxybenzoate.

According to a particular embodiment, the formate ester of formula (III) are selected from the group consisting of 4-allyl-2-methoxyphenyl formate, 2-methoxy-4-(prop-1-en-1-yl)phenyl formate, 2-methoxy-4-propylphenyl formate, 4-formyl-2-methoxyphenyl formate, 2-ethoxy-4-formylphenyl formate, 4-(3-oxobutyl)phenyl formate, 2-methoxyphenyl formate, 4-methylphenyl formate, 2-methylphenyl formate, 4-ethylphenyl formate, 2-ethylphenyl formate, 4-vinylphenyl formate, 2-propylphenyl formate, 2-acetylphenyl formate, 2-methoxy-4-(3-oxobutyl)phenyl formate, 2-methoxy-4-methylphenyl formate, 2-methoxy-4-vinylphenyl formate, 4-ethyl-2-methoxyphenyl formate, 2-ethoxy-4-methylphenyl formate, 4-methyl-2-propionylphenyl formate, methyl 2-(formyloxy)-5-methylbenzoate, ethyl 2-(formyloxy)-5-methylbenzoate, 2-ethoxy-4-(methoxymethyl)phenyl formate, 2-methoxy-4-(methoxymethyl)phenyl formate, 2-ethoxy-4-(ethoxymethyl)phenyl formate, 2-methoxy-4-(4-methyl-3,6-dihydro-2H-pyran-2-yl)phenyl formate, 2-methoxy-4-(4-methylenetetrahydro-2H-pyran-2-yl)phenyl formate, methyl 4-(formyloxy)-3-methoxybenzoate, ethyl 4-(formyloxy)-3-methoxybenzoate, methyl 2-(formyloxy)benzoate, ethyl 2-(formyloxy)benzoate, isobutyl 2-(formyloxy)benzoate, pentyl 2-(formyloxy)benzoate, isoamyl 2-(formyloxy)benzoate, 2-methylbutyl 2-(formyloxy)benzoate, cyclohexyl 2-(formyloxy)benzoate, (Z)-hex-3-en-1-yl 2-(formyloxy)benzoate, 4-methylpent-4-en-2-yl 2-(formyloxy)benzoate, phenethyl 2-(formyloxy)benzoate, 3-methyl-2-hexenyl 2-(formyloxy)benzoate, hexyl 2-(formyloxy)benzoate, benzyl 2-(formyloxy)benzoate, 3-methoxy-5-methylphenyl formate, 2-methoxy-5-(prop-1-en-1-yl)phenyl formate, 2-isopropyl-5-methylphenyl formate, 5-isopropyl-2-methylphenyl formate, 4-(hydroxymethyl)-2-methoxyphenyl formate and 3-methoxy-5-methylphenyl formate.

According to a particular embodiment, the alcohol of formula (IV) is selected from the group consisting of eugenol, isoeugenol, dihydroeugenol, vanillin, ethyl vanillin, 4-(4-hydroxyphenyl)butan-2-one, 2-hydroxy-4-methoxybenzaldehyde, 2-methoxyphenol, 4-methylphenol, 2-methylphenol, 4-ethylphenol, 2-ethylphenol, 4-vinylphenol, 2-propylphenol, 3-propylphenol, 1-(2-hydroxyphenyl)ethan-1-one, 4-(4-hydroxyl-3-methoxyphenyl)butan-2-one, 2-methoxy-4-methylphenol, 2-methoxy-4-vinylphenol, 4-ethyl-2-methoxyphenol, 2-ethoxy-4-methylphenol, 1-(2-hydroxy-5-methylphenyl)propan-1-one, methyl 2-hydroxy-5-methylbenzoate, ethyl 2-hydroxy-5-methylbenzoate, 2-ethoxy-4-(methoxymethyl)phenol, 2-methoxy-4-(methoxymethyl)phenol, 2-ethoxy-4-(ethoxymethyl)phenol, 2-methoxy-4-(4-methyl-3,6-dihydro-2H-pyran-2-yl)phenol, 2-methoxy-4-(4-methylenetetrahydro-2H-pyran-2-yl)phenol, methyl 4-hydroxy-3-methoxybenzoate, ethyl 4-hydroxy-3-methoxybenzoate, methyl salicylate, ethyl salicylate, isobutyl salicylate, pentyl salicylate, isoamyl salicylate, 2-methylbutyl salicylate, cyclohexyl salicylate, (Z)-hex-3-en-1-yl salicylate, 4-methylpent-4-en-2-yl salicylate, phenethyl salicylate, 3-methyl-2-hexenyl salicylate, hexyl salicylate, benzyl salicylate, 3-methoxy-5-methylphenol, 2-methoxy-5-(prop-1-en-1-yl)phenol, 2-isopropyl-5-methylphenol, 5-isopropyl-2-methylphenol, 4-(hydroxymethyl)-2-methoxyphenol and 3-methoxy-5-methylphenol.

Particularly, the alcohol of formula (IV) is selected from the group consisting of eugenol, isoeugenol, dihydroeugenol, 4-(4-hydroxyphenyl)butan-2-one, vanillin, (Z)-hex-3-en-1-yl salicylate, methyl salicylate, cyclohexyl salicylate, methyl 4-hydroxy-3-methoxybenzoate, 2-ethoxy-4-(methoxymethyl)phenol, 2-ethoxy-4-methylphenol, and 4-(hydroxymethyl)-2-methoxyphenol. 2-isopropyl-5-methylphenol According to a particular embodiment, the compound of formula (I) is selected from the group consisting of 4-allyl-2-methoxy-1-((2-phenylprop-1-en-1-yl)oxy)benzene, 2-methoxy-1-((2-phenylprop-1-en-1-yl)oxy)-4-((E)-prop-1-en-1-yl)benzene, 2-methoxy-1-((2-phenylprop-1-en-1-yl)oxy)-4-propylbenzene, 4-(4-((2-phenylprop-1-en-1-yl)oxy)phenyl)butan-2-one, 1-((2-ethyl-4,4-dimethylcyclohexylidene)methoxy)-2-methoxy-4-propylbenzene, 2-methoxy-1-((2-pentylcyclopentylidene)methoxy)-4-propylbenzene, 2-methoxy-1-((4-(tert-pentyl)cyclohexylidene)methoxy)-4-propylbenzene, 4-allyl-2-methoxy-1-((4-(tert-pentyl)cyclohexylidene)methoxy)benzene, 4-allyl-2-methoxy-1-((2-methylundec-1-en-1-yl)oxy)benzene, 2-methoxy-1-((2-methylundec-1-en-1-yl)oxy)-4-propylbenzene, 4-(4-((2-ethylhex-1-en-1-yl)oxy)phenyl)butan-2-one, 4-allyl-2-methoxy-1-((2-methoxy-2-phenylvinyl)oxy)benzene, 2-methoxy-1-((2-methoxy-2-phenylvinyl)oxy)-4-propylbenzene, methyl 2-((2-methoxy-2-phenylvinyl)oxy)benzoate, methyl 3-methoxy-4-((2-methoxy-2-phenylvinyl)oxy)benzoate, 2-ethoxy-1-((2-methoxy-2-phenylvinyl)oxy)-4-(methoxymethyl)benzene, 2-ethoxy-1-((2-methoxy-2-phenylvinyl)oxy)-4-methylbenzene, 2-methoxy-1-((2-methoxy-2-(p-tolyl)vinyl)oxy)-4-propylbenzene, 2-methoxy-1-((2-methoxy-2-(4-methoxyphenyl)vinyl)oxy)-4-propylbenzene, (Z)-hex-3-en-1-yl 2-((2-methoxy-2-phenylvinyl)oxy)benzoate, 3-methoxy-4-((2-methoxy-2-phenylvinyl)oxy)benzaldehyde, 1-((2-butoxy-2-phenylvinyl)oxy)-2-methoxy-4-propylbenzene, 2-methoxy-1-((2-(octyloxy)-2-phenylvinyl)oxy)-4-propylbenzene, 1-((2-(((Z)-hex-3-en-1-yl)oxy)-2-phenylvinyl)oxy)-2-methoxy-4-propylbenzene, 2-methoxy-1-((2-phenethoxy-2-phenylvinyl)oxy)-4-propylbenzene, 2-ethoxy-1-((2-ethoxy-2-phenylvinyl)oxy)-4-methylbenzene, methyl 4-((2-(hexyloxy)-2-phenylvinyl)oxy)-3-methoxybenzoate, (4-((2-(hexyloxy)-2-phenylvinyl)oxy)-3-methoxyphenyl)methanol, 4-((2-(hexyloxy)-2-phenylvinyl)oxy)-3-methoxybenzaldehyde, methyl 2-((2-(((Z)-hex-3-en-1-yl)oxy)-2-phenylvinyl)oxy)benzoate, (Z)-hex-3-en-1-yl 2-((2-(((Z)-hex-3-en-1-yl)oxy)-2-phenylvinyl)oxy)benzoate, (3-methoxy-4-((2-methoxy-2-phenylvinyl)oxy)phenyl)methanol, 1-isopropyl-4-methyl-2-((2-pentylcyclopentylidene)methoxy)benzene, 1-isopropyl-2-((2-methoxy-2-phenylvinyl)oxy)-4-methylbenzene, cyclohexyl 2-((2-methoxy-2-phenylvinyl)oxy)benzoate, According to any one of the above embodiment, the carbonyl compound of formula (II), the formate ester of formula (III) and the alcohol of formula (IV) are released from the precursor compound of formula (I) via oxidation of the precursor compound of formula (I) under ambient conditions. Even more, the precursor compound of formula (I) is oxidized under ambient conditions and in absence of any catalyst. For the sake of clarity, by the expression "ambient conditions", or the similar, it is meant the normal meaning understood by a person skilled in the art, i.e. the oxidation occurs at room temperature, under air and atmospheric pressure. In other words, the environment wherein the compound is oxidized is air. Herewith it is understood, that the compound of formula (I) is oxidized in ambient air. In particular, it is understood that the compound of formula (I) does not require a pure oxygen environment, heat or catalyst to be oxidized.

Without intending to be limited to any particular theory, the rate at which the precursor compound of formula (I) is oxidized may be greater than, equal to, or slower than the evaporation rates of the individual carbonyl compound of formula (II), the formate esters of formula (III) or the alcohols of formula (IV).

In some embodiments, the rate at which the precursor compound of formula (I) is oxidized, and thereby, the rate at which the individual carbonyl compound of formula (II), the formate esters of formula (III) or the alcohols of formula (IV) are released intensifies or prolongs the diffusion effect, and/or perception of the characteristic fragrance of at least one carbonyl compound formula (II), of at least one formate ester of formula (III) and/or of at least one alcohol of formula (IV) as defined above.

In one embodiment, 100% of the compound of formula (I) is oxidized in ambient air in a period of time ranging from 24 to 48 hours. Alternatively, 90% of the compound of formula (I) is oxidized in ambient air in a period of time ranging from 24 to 48 hours. Alternatively, 80% of the compound of formula (I) is oxidized in ambient air in a period of time ranging from 24 to 48 hours. Alternatively, 70% of the compound of formula (I) is oxidized in ambient air in a period of time ranging from 24 to 48 hours. Alternatively, 60% of the compound of formula (I) is oxidized in ambient air in a period of time ranging from 24 to 48 hours. Alternatively, 50% of the compound of formula (I) is oxidized in ambient air in a period of time ranging from 24 to 48 hours. Alternatively, 40% of the compound of formula (I) is oxidized in ambient air in a period of time ranging from 24 to 48 hours. Alternatively, 30% of the compound of formula (I) is oxidized in ambient air in a period of time ranging from 24 to 48 hours. Alternatively, 20% of the compound of formula (I) is oxidized in ambient air in a period of time ranging from 24 to 48 hours. Alternatively, 10% of the compound of formula (I) is oxidized in ambient air in a period of time ranging from 24 to 48 hours. Alternatively, 9% of the compound of formula (I) is oxidized in ambient air in a period of time ranging from 24 to 48 hours. Alternatively, 8% of the compound of formula (I) is oxidized in ambient air in a period of time ranging from 24 to 48 hours. Alternatively, 7% of the compound of formula (I) is oxidized in ambient air in a period of time ranging from 24 to 48 hours. Alternatively, 6% of the compound of formula (I) is oxidized in ambient air in a period of time ranging from 24 to 48 hours. Alternatively, 5% of the compound of formula (I) is oxidized in ambient air in a period of time ranging from 24 to 48 hours. Alternatively, 4% of the compound of formula (I) is oxidized in ambient air in a period of time ranging from 24 to 48 hours. Alternatively, 3% of the compound of formula (I) is oxidized in ambient air in a period of time ranging from 24 to 48 hours. Alternatively, 2% of the compound of formula (I) is oxidized in ambient air in a period of time ranging from 24 to 48 hours. Alternatively, 1% of the compound of formula (I) is oxidized in ambient air in a period of time ranging from 24 to 48 hours.

In a particular embodiment, the compound of formula (I) is encapsulated. The compound of formula (I) can be encapsulated in a microcapsule. In a preferred embodiment, the compound of formula (I) is encapsulated in a core-shell microcapsule wherein the compound of formula (I) is contained in the core surrounded by the shell. The shell of the microcapsule protects the compound of formula (I) from the environment. The shell is made of material which is able to release the compound of formula (I) and/or the compound of formulas (II), (III) and/or (IV). In a preferred embodiment, the shell is made of material which is able to release the compound of formula (I) and/or the compound of formulas (II), (III) and/or (IV) upon breakage of the shell and/or by diffusion through the shell. A person skilled in the art is well aware of processes to prepare said microcapsules. So microcapsule comprising at least one compound of formula (I) is one object of the present invention.

In a preferred embodiment, encapsulation of a compound of formula (I) may provide an environment within the capsule wherein all, or a portion of the compound of formula (I) may oxidize, thereby releasing the individual ketone of formula (II), the formate esters of formula (III) or the alcohols of formula (IV) into the capsule. In a preferred embodiment, the shell of the microcapsule may act as a permeability barrier, preventing the leakage of the individual carbonyl compound of formula (II), the formate esters of formula (III) or the alcohols of formula (IV) from the capsule.

In a second aspect, the present invention relates to a method to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined above. The term "surface", as used herein may refer to a user's skin, hair, a textile, or hard surface, on to which, a perfume composition comprising or containing the at least one compound of formula (I) is applied.

In a third aspect, the present invention relates to a method for intensifying or prolonging the diffusion effect of the characteristic fragrance of at least one carbonyl compound of formula (II), of at least one formate ester of formula (III) and/or of at least one alcohol of formula (IV) as defined above, on a surface or the air surrounding the perfuming composition, wherein the surface, or the air is treated with at least one compound (I) as defined above, or with a composition or article containing at least one compound (I), under conditions susceptible of allowing the release of at least one carbonyl compound formula (II), of at least one formate ester of formula (III) and/or of at least one alcohol of formula (IV) over time.

Moreover, the present invention relates to a perfuming composition comprising
i) at least one compound of formula (I), as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylene diisocyanate or a Biuret of hexamethylene diisocyanate or a trimer of xylene diisocyanate with trimethylolpropane (known with the tradename of Takenate®, origin: Mitsui Chemicals), among which a trimer of xylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

The term "perfumery base" is understood as a composition comprising at least one perfuming co-ingredient.

The perfuming co-ingredient is not a compound according to the invention. Moreover, the term "perfuming co-ingredient" is understood as a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpene hydrocarbons, nitrogenous or *sulphurous* heterocyclic compounds and essential oils, and the perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: *eucalyptus* oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients:methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2- buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl) propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecane-dione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cyclohepta-decen-1-one, 2-{1S)-1-[(1R)-3,3-dimethylcyclo-hexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclo-hexyl)ethoxycarbonyl]methyl propanoate;

Woody ingredients: 1-[(1RS,6SR)-2,2,6-trimethylcy-clohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naph-tho[2,1-b]furan and any of its stereoisomers, heliotropin, anisic aldehyde, eugenol, cinnamic aldehyde, clove oil, 3-(1,3-benzodioxol-5-yl)-2-methyl-propanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

The term "perfumery adjuvant" is understood as an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one of the invention's compounds of formula (I) and at least one perfumery carrier represents a particular embodiment of the invention as well as a perfuming composition comprising at least one of the invention's compounds, at least one perfumery carrier, at least one perfumery base, and optionally at least one perfumery adjuvant.

It is useful to mention here that the possibility to have, in the compositions mentioned above, more than one of the invention's compounds or other precursors of similar type is important as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compounds can also be advantageously used in all the fields of modem perfumery, i.e. fine or functional perfumery, to positively impart or modify the odor of a consumer product into which the compound (I) is added. Therefore, the present invention also relates to a perfumed consumer product comprising at least one compound of formula (I), as defined above or a perfuming composition as defined above.

For the sake of clarity, it has to be mentioned that, the term "perfumed consumer product" is understood as a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

In one embodiment, the perfumed consumer product is a perfume, a fabric care product, a body-care product, a cosmetic preparation, a skin-care product, an air care product or a home care product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furniture care product, a wipe, a dish detergent or a hard-surface (e.g. a floor, bath, sanitary or a window-cleaning) detergent; a leather care product; a car care product, such as a polish, a wax or a plastic cleaner.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, New Jersey (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. In the case of perfumed consumer product, typical concentrations are in the order of 0.001% to 5% by weight, or even more, of the compounds of the invention based on the weight of the consumer product into which they are incorporated.

Moreover, the present invention relates to a compound of formula (I). So another object of the invention is a compound of formula

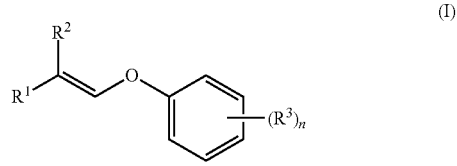

in the form of any one of its stereoisomers or a mixture thereof and wherein when $R^2$ represents a $OR^{2'}$ wherein $R^{2'}$ represents a $C_{1-12}$ alkyl group, a $C_{3-12}$ alkenyl group, a phenethyl group or a benzyl group, then $R^1$ is a phenyl group optionally substituted by one or two $R^{1'}$ group wherein $R^{1'}$, simultaneously or independently, represents a hydroxyl group, a $C_{1-3}$ alkyl group, a $C_{1-3}$ alkoxy group or a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring;

when $R^2$ represents a $C_{1-3}$ alkyl, then $R^1$ represents a $C_{1-15}$ alkyl, $C_{2-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom; n represent an integer between 1 and 3;

$R^3$, simultaneously or independently, represents at least one substituent of the aromatic ring and is a $C_{1-8}$ alkyl group optionally substituted by a $C_{1-6}$ alkoxy, or an oxo group, a $C_{2-6}$ alkenyl group, a $C_{1-6}$ alkoxy group or a $R^bOCO$ group wherein $R^b$ is a hydrogen atom, a $C_{1-7}$ alkyl group, a $C_{2-7}$ alkenyl group, a $C_{3-7}$ cycloalkyl group, a benzyl group or a phenethyl group; provided that when $R^1$ is methyl then $R^2$ is not methyl,
when $R^1$ is ethyl then $R^2$ is not ethyl,
1,3-dimethoxy-2-((2-phenylprop-1-en-1-yl)oxy)benzene, 1-methyl-4-((-2-methyl-4-(2,6,6-trimethylcyclohex-1-en-1-yl)buta-1,3-dien-1-yl)oxy)benzene, 1-methyl-4-((-2-methyl-4-(2,6,6-trimethylcyclohex-2-en-1-yl)buta-1,3-dien-1-yl)oxy)benzene and 1,2-dimethoxy-4-(1-(2-methoxyphenoxy)prop-1-en-2-yl)benzene are excluded.

In a further aspect, the present invention also relates to the use of precursor compounds for releasing compounds selected from the group consisting of
a) a carbonyl compound of formula

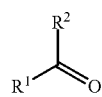

(II)

wherein when $R^2$ represents a $OR^{2'}$ wherein $R^{2'}$ represents a $C_{1-6}$ alkyl group, a $C_{2-6}$ alkenyl group or a benzyl group, then $R^1$ is a phenyl group optionally substituted by one or two $R^{1'}$ group wherein $R^{1'}$, simultaneously or independently, represents a hydroxyl group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring;

when $R^2$ represents a $C_{1-6}$ alkyl or a $C_{6-10}$ aryl group each optionally substituted by a hydroxyl group, a $C_{1-3}$ alkyl group, a $C_{1-3}$ alkoxy group, then $R^1$ represents a $C_{1-15}$ alkyl, $C_{2-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula

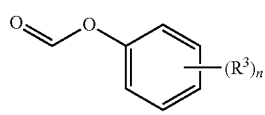

(III)

wherein n represent an integer between 1 and 5;
$R^3$, simultaneously or independently, represents at least one substituent of the aromatic ring and is a $C_{1-6}$ alkyl group optionally substituted by a hydroxy, a $C_{1-6}$ alkoxy or an oxo group; a $C_{4-7}$ oxacycloalkyl or oxacycloalkenyl group optionally substituted with a $C_{1-3}$ alkyl or a methylene group; a $C_{2-6}$ alkenyl group; a $C_{1-6}$ alkoxy group; or a $R^bOCO$ group wherein $R^b$ is a hydrogen atom, a $C_{1-7}$ alkyl group, a $C_{2-7}$ alkenyl group, a $C_{3-7}$ cycloalkyl group, a benzyl group or a phenethyl group;

c) an alcohol of formula

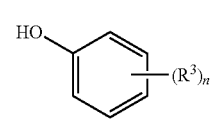

(IV)

wherein $R^3$ has the same meaning as defined above;
wherein at least one of the compounds of formula (II), (III) or (IV) is an active compound;
wherein the precursor compound comprises a compound of formula (I)

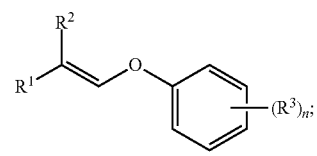

(I)

wherein n, $R^1$, $R^2$ and $R^3$ have the same meaning as defined above; by exposing the precursor compound of formula (I) to an environment wherein the compound is oxidized; i.e. ambient conditions.

In a further aspect, the present invention relates to the use of at least one compound of formula (I) as defined above to confer, enhance, improve or modify the odor properties of a perfuming composition, the air surrounding the perfuming composition, a surface, or of a perfumed article, comprising adding to the composition or article or contacting or treating the surface with an effective amount of at least one compound of formula (I) as defined above. The term "surface", as used herein may refer to a user's skin, hair, a textile, or hard surface, on to which, a perfume composition comprising or containing the at least one compound of formula (I) is applied.

In a further aspect, the present invention relates to the use of at least one compound of formula (I) as defined above for intensifying or prolonging the diffusion effect, and/or perception of the characteristic fragrance of at least one carbonyl compound formula (II), of at least one formate ester of formula (III) and/or of at least one alcohol of formula (IV) as defined above, on a surface, wherein the surface is treated with at least one compound of formula (I) as defined above, or with a composition or article containing the at least one compound of formula (I), under conditions susceptible of allowing the release of the at least one carbonyl compound formula (II), of at least one formate ester of formula (III) and/or of at least one active alcohol of formula (IV) over time.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; $CH_2$, methylene; $CH_3$, methyl.

Example 1

Preparation of Compounds According to Formula (I) Releasing a Carbonyl Compound of Formula (II) being a Ketone General Experimental Part for Compounds 1 Through 7

A dimethyl acetal (3 equiv) was combined with a phenol (1 equiv) and $KHSO_4$ (0.12-0.15 equiv) in a round-bottomed flask (100 mL) equipped with a distillation head and nitrogen bubbler. The mixture was carefully, lowered into an oil bath preheated to 175° C. The oil bath temperature was maintained for about 10-20 minutes to allow for an initial, vigorous distillation of methanol and then increased to 220° C. while continuing the removal of methanol. After 3-4 h of heating, the mixture was removed from the oil bath and $Na_2CO_3$ (2 g) was added. The resulting enol ethers were isolated by short-path, vacuum distillation from the reaction flask.

Compound 1. 4-allyl-2-methoxy-1-((2-phenylprop-1-en-1-yl)oxy)benzene: Starting from eugenol (10 g, 61 mmol), the dimethyl acetal of 2-phenylpropanal (32.9 g, 183 mmol) and $KHSO_4$ (0.996 g, 7.31 mmol), the title compound (10.71 g, 38.2 mmol) was isolated by distillation (bp 160-165° C., 3.3 Pa) as a pale yellow oil in 63% yield (E/Z=78:22).$^1$H NMR ($CDCl_3$, 500 MHz, E-isomer): δ 2.16 (d, J=1.4 Hz, 3H), 3.35 (d, J=6.7 Hz, 2H), 3.88 (s, 3H), 5.05-5.09, 5.09-5.12 (m, 2H), 5.96 (ddt, J=17.0, 10.2, 6.7 Hz, 1H), 6.71 (dd, J=8.1, 1.9 Hz, 1H), 6.73 (q, J=1.3 Hz, 1H), 6.77 (d, J=8.1 Hz, 1H), 6.94 (d, 8.1 Hz, 1H), 7.17-7.25 (m, 1H), 7.28-7.34 (m, 2H), 7.35-7.39 (m, 2H).

$^{13}$C NMR ($CD_2Cl_2$, 125 MHz, E-isomer): δ 13.1 ($CH_3$), 39.9 ($CH_2$), 56.1 ($CH_3$), 112.9 (CH), 115.9 ($CH_2$), 117.0 (CH), 120.2 (C), 120.7 (CH), 125.5 (CH), 126.6 (CH), 128.4 (CH), 135.4 (C), 137.4 (CH), 140.0 (C), 140.3 (CH), 145.4 (C), 149.6 (C).

Compound 2. 2-methoxy-1-((2-phenylprop-1-en-1-yl)oxy)-4-((E)-prop-1-en-1-yl)benzene: Starting from isoeugenol (10 g, 61 mmol), the dimethyl acetal of 2-phenylpropanal (32.9 g, 183 mmol) and $KHSO_4$ (0.996 g, 7.31 mmol), the title compound (8.34 g, 29.7 mmol) was isolated by distillation (bp 170-180° C., 3.3 Pa) as a pale yellow oil in 41% yield (E/Z=78:22).$^1$H NMR ($CDCl_3$, 500 MHz, E-isomer): δ 1,87 (d, J=6.6 Hz, 3H), 2.16 (d, J=1.4 Hz, 3H), 3.90 (s, 3H), 6.14 (dq, J=15.7, 6.6 Hz, 1H), 6.34 (dq, J=15.7, 1.6 Hz, 1H), 6.74 (q, J=1.4 Hz, 1H), 6.84 (dd, J=8.2, 1.9 Hz, 1H), 6.92 (d, J=8.2 Hz, 1H), 6.93 (d, J=1.9 Hz, 1H), 7.18-7.25 (m, 1H), 7.29-7.34 (m, 2H), 7.36-7.40 (m, 2H).

$^{13}$C NMR ($CD_2Cl_2$, 125 MHz, E-isomer): δ 13.1 ($CH_3$), 18.4 ($CH_3$), 56.1 ($CH_3$), 109.7 (CH), 116.8 (CH), 118.6 (CH), 120.5 (C), 124.9 (CH), 125.5 (CH), 126.6 (CH), 128.4 (CH), 130.5 (CH), 133.6 (C), 139.9 (C), 140.0 (CH), 146.1 (C), 149.6 (C).

Compound 3. 2-methoxy-1-((2-phenylprop-1-en-1-yl)oxy)-4-propylbenzene: Starting from dihydroeugenol (10 g, 60 mmol), the dimethyl acetal of 2-phenylpropanal (32.5 g, 180 mmol) and $KHSO_4$ (0.984 g, 7.23 mmol), the title compound (13.6 g, 48.3 mmol) was isolated by distillation (bp 145-155° C., 3.3 Pa) as a pale yellow oil in 80% yield (E/Z=78:22). $^1$H NMR ($CDCl_3$, 500 MHz, E-isomer): δ 0.94 (t, J=7.4 Hz, 3H), 1.63 (sextet, J=7.5 Hz, 2H), 2.16 (d, J=1.4 Hz, 3H), 2.55 (t, J=7.6 Hz, 2H), 3.88 (s, 3H), 6.70 (dd, J=8.1, 1.9 Hz, 1H), 6.74 (q, J=1.4 Hz, 1H), 6.77 (d, J=1.9 Hz, 1H), 6.92 (d, J=8.1 Hz, 1H), 7.18-7.24 (m, 1H), 7.28-7.33 (m, 2H), 7.36-7.39 (m, 2H).

$^{13}$C NMR ($CD_2Cl_2$, 125 MHz, E-isomer): δ 13.1 ($CH_3$), 13.8 ($CH_3$), 24.7 ($CH_2$), 37.8 ($CH_2$), 56.1 ($CH_3$), 112.9 (CH), 116.9 (CH), 119.9 (C), 120.5 (CH), 125.5 (CH), 126.5 (CH), 128.4 (CH), 138.2 (C), 140.0 (C), 140.5 (CH), 145.1 (C), 149.4 (C).

Compound 4. 4-(4-((2-phenylprop-1-en-1-yl)oxy)phenyl)butan-2-one: Starting from 4-(4-hydroxyphenyl)butan-2-one (raspberry ketone) (10 g, 61 mmol), the dimethyl acetal of 2-phenylpropanal (32.9 g, 183 mmol) and $KHSO_4$ (0.996 g, 7.31 mmol), the title compound (6.07 g, 21.6 mmol) was isolated by distillation (bp>180° C., 3.3 Pa) as a pale yellow oil in 36% yield (E/Z=78:22).$^1$H NMR ($CDCl_3$, 500 MHz, E-isomer): δ 2.12 (s, 3H), (d, J=1.6 Hz, 3H), 2.72 (t, J=7.5 Hz, 2H), 2.85 (t, J=7.5 Hz, 2H), 6.81 (q, J=1.3 Hz, 1H), 6.97 (d, 8.5 Hz, 2H), 7.13 (d, J=8.5 Hz, 2H), 7.20-7.26 (m, 1H), 7.30-7.35 (m, 2H), 7.36-7.40 (m, 2H).

$^{13}$C NMR ($CD_2Cl_2$, 125 MHz, E-isomer): δ 13.0 ($CH_3$), 28.9 ($CH_2$), 30.1 ($CH_3$), 45.3 ($CH_2$), 116.4 (CH), 120.2 (C), 125.4 (CH), 126.7 (CH), 128.5 (CH), 129.4 (CH), 135.3 (C), 139.2 (CH), 139.8 (C), 156.0 (C), 207.9 (C).

Compound 5. 4-allyl-2-methoxy-1-((2-methylundec-1-en-1-yl)oxy)benzene: Starting from eugenol (8.02 g, 48.8 mmol), the dimethyl acetal of 2-methylundecanal (33.7 g, 146 mmol) and $KHSO_4$ (0.996 g, 7.31 mmol), the title compound (7.15 g, 21.6 mmol) was isolated by distillation (bp>165° C., 3.3 Pa) as a pale yellow oil in 44% yield (E/Z=60:40). $^1$H NMR ($CDCl_3$, 500 MHz, E-isomer): δ 0.88 (t, J=6.9 Hz, 3H), 1.19-1.33 (m, 12H), 1.38-1.46 (m, 2H), 1.71 (d, J=1.3 Hz, 3H), 1.99 (t, J=7.4 Hz, 2H), 3.33 (d, J=7.0 Hz, 2H), 3.86 (s, 3H), 5.03-5.08, 5.08-5.11 (m, 2H), 5.95 (ddt, J=17.0, 10.2, 6.8 Hz, 1H), 6.11 (q, J=1.3 Hz, 1H), 6.69 (d, J=8.1 Hz, 1H), 6.73 (d, J=2.1 Hz, 1H), 6.85 (d, J=8.1 Hz, 1H).

$^{13}$C NMR ($CD_2Cl_2$, 125 MHz, E-isomer): δ 13.2 ($CH_3$), 14.1 ($CH_3$), 22.7 ($CH_2$), 27.7 ($CH_2$), 29.2 ($CH_2$), 29.4 ($CH_2$), 29.5 ($CH_2$), 29.6 ($CH_2$), 31.9 ($CH_2$), 33.8 ($CH_2$), 39.9 ($CH_2$), 56.0 ($CH_3$), 112.7 (CH), 115.6 (CH), 115.7 ($CH_2$), 120.5 (C), 121.8 (C), 134.3 (C), 136.2 (CH), 137.7 (CH), 145.7 (C), 149.2 (C).

Compound 6. 2-methoxy-1-((2-methylundec-1-en-1-yl)oxy)-4-propylbenzene: Starting from dihydroeugenol (10 g, 60.2 mmol), the dimethyl acetal of 2-methylundecanal (41.6 g, 181 mmol) and $KHSO_4$ (1.23 g, 9.04 mmol), the title compound (9.07 g, 27.3 mmol) was isolated by distillation (bp>165° C., 3.3 Pa) as a pale yellow oil in 45% yield (E/Z=58:42).

$^1$H NMR ($CDCl_3$, 500 MHz, E-isomer): δ 0.88 (t, J=6.9 Hz, 3H), 0.94 (t, J=7.4 Hz, 3H), 1.20-1.34 (m, 12H), 1.38-1.47 (m, 2H), 1.62 (sextet, J=7.5 Hz, 2H), 1.71 (d, J=1.3 Hz, 3H), 1.98 (t, J=7.4 Hz, 2H), 2.53 (t, J=7.6 Hz, 2H), 3.87 (s, 3H), 6.11 (q, J=1.3 Hz, 1H), 6.68 (d, J=8.1 Hz, 1H), 6.73 (d, 2.1 Hz, 1H), 6.83 (d, J=8.1 Hz, 1H).

¹³C NMR (CD$_2$Cl$_2$, 125 MHz, E-isomer): δ 13.2 (CH$_3$), 13.8 (CH$_3$), 14.1 (CH$_3$), 22.7 (CH$_2$), 24.7 (CH$_2$), 27.8 (CH$_2$), 29.2 (CH$_2$), 29.4 (CH$_2$), 29.5 (CH$_2$), 29.6 (CH$_2$), 31.9 (CH$_2$), 33.8 (CH$_2$), 37.8 (CH$_2$), 56.0 (CH$_3$), 112.7 (CH), 115.6 (CH), 120.3 (CH), 121.5 (C), 136.4 (CH), 137.0 (C), 145.3 (C), 149.1 (C).

Compound 7. 4-(4-((2-ethylhex-1-en-1-yl)oxy)phenyl)butan-2-one: Starting from 4-(4-hydroxyphenyl)butan-2-one (raspberry ketone) (10 g, 61 mmol), the dimethyl acetal of 2-ethylhexanal (31.8 g, 182 mmol) and KHSO$_4$ (0.998 g, 7.33 mmol), the title compound (2.26 g, 21.6 mmol) was isolated by distillation (bp 145-155° C., 6.7 Pa) as a colorless liquid in 14% yield (isomer ratio=53:47).

¹H NMR (CDCl$_3$, 600 MHz, major isomer): δ 0.89 (t, J=7.2 Hz, 3H), 1.05 (t, J=7.4 Hz, 3H), 1.27-1.45 (m, 4H), 2.02 (t, J=7.6 Hz, 2H), 2.13 (s, 3H), 2.17 (q, J=7.5 Hz, 2H), 2.72 (t, J=7.6 Hz, 2H), 2.84 (t, J=7.6 Hz, 2H), 6.17 (s, 1H), 6.88 (d, J=8.5 Hz, 2H), 7.09 (d, J=8.5 Hz, 2H).

¹³C NMR (CD$_2$Cl$_2$, 150 MHz, isomer mixture): δ 12.6 (CH$_3$), 13.0 (CH$_3$), 14.0 (CH$_3$), 20.2 (CH$_2$), 22.4 (CH$_2$), 22.6 (CH$_2$), 24.6 (CH$_2$), 26.7 (CH$_2$), 29.0 (CH$_2$), 29.9 (CH$_2$), 30.1 (CH$_3$), 30.1 (CH$_2$), 30.8 (CH$_2$), 45.4 (CH$_2$), 115.9 (CH), 116.0 (CH), 127.1 (C), 127.2 (C), 129.2 (CH), 129.3 (CH), 134.3 (CH), 135.3 (CH), 135.4 (CH), 156.3 (C), 156.4 (C), 208.1 (C).

General Experimental Part for Compounds 8 Through 12.

Methoxymethyltriphenylphosphonium chloride (15.1 g, 44.1 mmol) and the ketone (29.4 mmol) were added to 120 ml of toluene. Potassium t-butoxide (5.27 g, 47 mmol) was added to the stirring slurry in 4 portions every 15 min. The mixture was stirred for 4-24 h becoming a deep red color. It then was poured into 500 ml of water and extracted with EtOAc (3×250 mL). The organic phases were combined, dried over Na$_2$SO$_4$, filtered and concentrated during which triphenylphospine oxide would precipitate. The resulting methyl enol ether product was isolated by distillation either directly from the initial concentrate or after separating it from the precipitate by filtration and washing with diethyl ether. The isolated methyl enol ether (30-50 mmol) then was combined with dihyroeugenol, eugenol or 2-isopropy-5-methylphenol (1 equiv) and KHSO$_4$ (25 mole %) in a round-bottomed flask (25 mL) equipped with a distillation head and nitrogen bubbler. The mixture was lowered into an oil bath preheated to 180° C. The oil bath temperature was increased over 10-15 min to 220° C. while allowing liberated methanol to distill from the reaction mixture. After 1 h at 220° C., the mixture was removed from the oil bath and allowed to cool. The reaction mixture was placed under vacuum and heated to first distill unreacted starting materials and volatile by-products. The remaining reaction mixture was further heated (oil bath up to 220° C.) to distill the enol ethers. If necessary the distilled enol ether was further purified by Kugelrohr distillation or silica gel flash chromatography.

Compound 8. 1-((2-ethyl-4,4-dimethylcyclohexylidene)methoxy)-2-methoxy-4-propylbenzene: The title compound was prepared starting from 2-ethyl-4,4-dimethylcyclohexan-1-one. It was isolated by short-path distillation (bp 154-156° C., 2 Pa) from the crude reaction mixture as an amber oil in 35% yield (E/Z=80:20) from the intermediate methyl enol ether.

¹H NMR (CD$_2$Cl$_2$, 500 MHz, E-isomer): δ 0.88 (t, J=7.5 Hz, 1H), 0.93 (s, 3H), 0.93 (t, J=7.3 Hz, 3H), 0.95 (t, J=7.5 Hz, 3H), 1.00 (s, 3H), 1.18-1.28 (m, 2H), 1.40-1.50 (m, 1H), 1.56-1.69 (m, 4H), 1.86 (td, J=13.5, 4.0 Hz, 1H), 2.04 (sextet, J=5.6 Hz, 1H), 2.52 (t, J=7.5 Hz, 2H), 2.76 (dt, J=13.6, 3.7 Hz, 1H), 3.82 (s, 3H), 6.01 (s, 1H), 6.68 (d, J=8.0 Hz, 1H), 6.74 (s, 1H), 6.83 (d, 8.0 Hz, 1H).

¹³C NMR (CD$_2$Cl$_2$, 125 MHz, E-isomer): δ 12.2 (CH$_3$), 14.0 (CH$_3$), 22.5 (CH$_2$), 25.2 (CH$_2$), 25.4 (CH$_3$), 31.2 (C), 32.6 (CH$_3$), 38.1 (CH$_2$), 38.2 (CH$_2$), 40.6 (CH$_2$), 47.6 (CH$_2$), 56.3 (CH$_3$), 113.2 (CH), 116.1 (CH), 120.7 (CH), 128.4 (C), 133.6 (CH), 137.6 (C), 146.0 (C), 149.7 (C).

Compound 9. 2-methoxy-1-((2-pentylcyclopentylidene)methoxy)-4-propylbenzene: The title compound was prepared starting from 2-pentylcyclopentan-1-one. It was isolated by short-path distillation (bp 158-165° C., 2 Pa) from the crude reaction mixture as an amber oil in 27% yield from the intermediate methyl enol ether (E/Z=60:40).

¹H NMR (CD$_2$Cl$_2$, 600 MHz, E-isomer): δ 0.89 (t, J=7.0 Hz, 3H), 0.93 (t, J=7.3 Hz, 3H), 1.20-1.46 (m, 8H), 1.49-1.58 (m, 2H), 1.61 (sextet, J=7.5 Hz, 2H), 1.69-1.79 (m, 1H), 1.81-1.92 (m, 1H), 2.32-2.39 (m, 1H), 2.42-2.50 (m, 2H), 2.52 (t, J=7.6 Hz, 2H), 3.82 (s, 3H), 6.17 (q, J=2.3 Hz, 1H), 6.68 (dd, J=8.1, 1.9 Hz, 1H), 6.74 (d, J=1.9 Hz, 1H), 6.83 (d, J=8.1 Hz, 1H).

¹³C NMR (CD$_2$Cl$_2$, 150 MHz, E-isomer): δ 14.0 (CH$_3$), 14.3 (CH$_3$), 23.1 (CH$_2$), 24.5 (CH$_2$), 25.2 (CH$_2$), 27.8 (CH$_2$), 27.9 (CH$_2$), 32.5 (CH$_2$), 33.6 (CH$_2$), 35.2 (CH$_2$), 38.1 (CH$_2$), 42.0 (CH), 56.3 (CH$_3$), 113.2 (CH), 116.4 (CH), 120.7 (CH), 131.4 (C), 135.1 (CH), 137.7 (C), 145.8 (C), 149.7 (C).

Compound 10. 2-methoxy-1-((4-(tert-pentyl)cyclohexylidene)methoxy)-4-propylbenzene: The title compound was prepared starting from 4-(tert-pentyl)cyclohexan-1-one. It was isolated by short-path distillation (bp=178-182° C., 2 Pa) from the crude reaction mixture. This material was subjected to Kugelrohr distillation (185-200° C., 2 Pa) to afford the final product as a colorless oil in 20% yield from the intermediate methyl enol ether.

¹H NMR (CD$_2$Cl$_2$, 600 MHz): δ 0.80 (s, 6H), 0.81 (t, J=7.5 Hz, 3H), 0.93 (t, J=7.4 Hz, 3H), 0.99-1.10 (m, 2H), 1.28 (m, 1H), 1.28 (q, J=7.4 Hz, 2H), 1.61 (sextet, J=7.6 Hz, 2H), 1.69 (bt, J=13.5 Hz, 1H), 1.78-1.87 (m, 2H), 1.96 (bt, J=13.5 Hz, 1H), 2.25 (bd, J=13.5 Hz, 1H), 2.52 (t, J=7.6 Hz, 2H), 2.93 (bd, J=13.5 Hz, 1H), 3.82 (s, 3H), 6.07 (t, J=1.8 Hz, 1H), 6.68 (dd, J=8.1, 1.9 Hz, 1H), 6.73 (d, J=1.9 Hz, 1H), 6.83 (d, J=8.1 Hz, 1H).

¹³C NMR (CD$_2$Cl$_2$, 150 MHz): δ 8.3 (CH$_3$), 14.0 (CH$_3$), 24.5 (CH$_3$), 25.2 (CH$_2$), 26.1 (CH$_2$), 27.8 (CH$_2$), 29.0 (CH$_2$), 30.9 (CH$_2$), 33.1 (CH$_2$), 35.1 (C), 38.1 (CH$_2$), 46.0 (CH), 56.3 (CH$_3$), 113.2 (CH), 115.1 (CH), 120.7 (CH), 125.0 (C), 133.5 (CH), 137.6 (C), 145.8 (C), 149.6 (C).

Compound 11. 4-allyl-2-methoxy-1-((4-(tert-pentyl)cyclohexylidene)methoxy)benzene: The title compound was prepared starting from 4-(tert-pentyl)cyclohexan-1-one. It was isolated by short-path distillation (bp=177-180° C., 2 Pa) from the crude reaction mixture. This material was subjected to silica gel flash chromatography (hexane/EtOAc, 99:1) to afford the final product as a colorless oil in 16% yield from the intermediate methyl enol ether.

¹H NMR (CDCl$_3$, 500 MHz): δ 0.79 (s, 6H), 0.80 (t, J=7.5 Hz, 3H), 1.06 (qt, J=12.6, 3.2 Hz, 2H), 1.22-1.28 (m, 1H), 1.26 (q, J=7.5 Hz, 2H), 1.69 (bt, J=13.4 Hz, 1H), 1.75-1.87 (m, 2H), 1.95 (bt, J=13.3 Hz, 1H), 2.26 (bd, J=13.6 Hz, 1H), 2.97 (bd, J=17.0, 1.7 Hz, 1H), 3.34 (d, J=6.7 Hz, 2H), 3.86 (s, 3H), 5.06 (dq, J=10.2, 1.3 Hz, 1H), 5.08 (dq, J=17.0, 1.7 Hz, 1H), 5.96 (ddt, J=17.0, 10.2, 6.7 Hz, 1H), 6.08 (t, J=1.7 Hz, 1H), 6.70 (dd, J=8.1, 1.9 Hz, 1H), 6.73 (d, J=1.9 Hz, 1H), 6.88 (d, J=8.1 Hz, 1H).

¹³C NMR (CDCl$_3$, 125 MHz): δ 8.2 (CH$_3$), 24.4 (CH$_3$), 25.8 (CH$_2$), 27.3 (CH$_2$), 28.5 (CH$_2$), 30.6 (CH$_2$), 32.7 (CH$_2$), 34.8 (C), 39.9 (CH$_2$), 45.5 (CH), 56.0 (CH$_3$), 112.6

(CH), 115.5 (CH), 115.7 (CH$_2$), 120.5 (CH), 1245.8 (C), 132.7 (CH), 134.3 (C), 137.6 (CH), 145.8 (C), 149.2 (C).

Compound 12. 1-isopropyl-4-methyl-2-((2-pentylcyclopentylidene)methoxy)benzene: The title compound was prepared starting from 2-pentylcyclopentan-1-one. It was isolated by short-path distillation (bp=152-162° C., 2 Pa) from the crude reaction mixture. This material was subjected to silica gel flash chromatography (hexane) followed by Kugelrohr distillation (185° C., 2.6 Pa) to afford the final product as a colorless oil in 16% yield from the intermediate methyl enol ether (E/Z=62:38).

$^1$H NMR (CDCl$_3$, 500 MHz, E-isomer): δ 0.90 (t, J=6.9 Hz, 3H), 1.22 (d, J=6.9 Hz, 6H), 1.23-1.48 (m, 8H), 1.51-1.62 (m, 2H), 1.69-1.81 (m, 1H), 1.85-1.97 (m, 1H), 2.30 (s, 3H), 2.34-2.44 (m, 1H), 2.44-2.55 (m, 2H), 3.29 (septet, J=6.9 Hz, 1H), 6.26 (q, J=2.0 Hz, 1H), 6.71 (s, 1H), 6.79 (d, J=7.7 Hz, 1H), 7.10 (d, J=7.7 Hz, 1H).

$^{13}$C NMR (CD$_2$Cl$_2$, 125 MHz, E-isomer): δ 14.1 (CH$_3$), 21.2 (CH$_3$), 22.7 (CH$_3$), 22.8 (CH$_2$), 24.1 (CH$_2$), 26.9 (CH), 27.5 (CH$_2$), 37.6 (CH$_2$), 32.1 (CH$_2$), 33.3 (CH$_2$), 34.8 (CH$_2$), 41.6 (CH), 115.1 (CH), 122.5 (CH), 126.1 (CH), 131.3 (C), 133.8 (CH), 134.4 (C), 136.4 (C), 155.1 (C).

Example 2

Preparation of Compounds According to Formula (I) Releasing a Carbonyl Compound of Formula (II) being an Ester
General Experimental Part for Compounds 13 Through 22

A mixture of a 2-bromoacetophenone (100 mmol), a phenol (130 mmol), K$_2$CO$_3$ (150 mmol) and acetone (250 ml) was heated at reflux for 3-4 h or stirred at room temperature for 1 day. After filtering the mixture through a bed of Celite®, the solution was concentrated. The resulting 2-phenoxyacetophenone was isolated by Kugelrohr distillation or by silica gel flash chromatography. The 2-phenoxyacetophenone was converted to the corresponding dimethyl acetal by mixing with trimethyl orthoformate (7-10 equiv.), methanol (200 ml) and p-toluene sulfonic acid (0.02 equiv.) and heating the solution at 70° C. for 6-8 h and then stirring at rt for 1 day. The mixtures were monitored by gas chromatography to ensure conversion to the acetal, although in a few cases complete conversion was not achieved. After adding solid Na$_2$CO$_3$ (0.06 equiv.), the mixture was concentrated under vacuum. The remaining residue was dissolved in diethyl ether and washed with water, sat. NH$_4$Cl and water. The organic phase was dried over Na$_2$SO$_4$, filtered and concentrated under vacuum. The resulting dimethyl acetal was used without further purification and was combined with KHSO$_4$ (0.01-0.02 equiv.) in a round-bottomed flask equipped with a distillation head. The mixture was placed under vacuum (1.5 kPa) and then heated with an oil bath at 140° C. for 1-2 h. The mixture was removed from the oil bath and Na$_2$CO$_3$ (0.2 g) was added. The reaction mixture was dissolved in diethyl ether and washed with sat. Na$_2$CO$_3$. The organic phase was dried over Na$_2$SO$_4$, filtered and concentrated under vacuum. The resulting enol ether was purified by distillation or silica gel flash chromatography.

Compound 13. 4-allyl-2-methoxy-1-((2-methoxy-2-phenylvinyl)oxy)benzene: Starting from 4-allyl-1-(2,2-dimethoxy-2-phenylethoxy)-2-methoxybenzene (5.5 g, 16.7 mmol) and KHSO$_4$ (0.17 mmol), the title compound (3.9 g, 15.1 mmol) was isolated by Kugelrohr distillation (195° C., 2.6 Pa) as a pale yellow oil in 79% yield (Z/E=64:36).

$^1$H NMR (CDCl$_3$, 500 MHz, Z-isomer): δ 3.35 (d, J=6.7 Hz, 2H), 3.83 (s, 3H), 3.88 (s, 3H), 5.05-5.09, 5.10-5.12 (m, 2H), 5.96 (ddt, J=16.9, 10.2, 6.7 Hz, 1H), 6.47 (s, 1H), 6.72 (dd, J=8, 1, 1.9 Hz, 1H), 6.77 (d, J=1.9 Hz, 1H), 7.00 (d, J=8.1 Hz, 1H), 7.24-7.29 (m, 1H), 7.30-7.36 (m, 2H), 7.44-7.48 (m, 2H).

$^{13}$C NMR (CDCl$_3$, 125 MHz, Z-isomer): δ 39.9 (CH$_2$), 56.0 (CH$_3$), 59.5 (CH$_3$), 112.8 (CH), 115.9 (CH$_2$), 116.6 (CH), 120.6 (CH), 125.1 (CH), 128.0 (CH), 128.4 (CH), 128.9 (CH), 134.3 (C), 135.4 (C), 137.4 (CH), 143.9 (C), 145.5 (C), 149.6 (C).

Compound 14. 2-methoxy-1-((2-methoxy-2-phenylvinyl)oxy)-4-propylbenzene: Starting from 1-(2,2-dimethoxy-2-phenylethoxy)-2-methoxy-4-propylbenzene (8 g, 24.2 mmol) and KHSO$_4$ (0.24 mmol), the title compound (4.5 g, 15.1 mmol) was isolated by Kugelrohr distillation (180-190° C., 4.0 Pa) as a yellow oil in 62% yield (Z/E=62:38).

$^1$H NMR (CDCl$_3$, 500 MHz, Z-isomer): δ 0.94 (t, J=7.42 Hz, 3H), 1.63 (sextet, J=7.6 Hz, 2H), 2.55 (t, J=7.6 Hz, 2H), 3.84 (s, 3H), 3.88 (s, 3H), 6.48 (s, 1H), 6.71 (dd, J=8.1, 1.9 Hz, 1H), 6.76 (d, J=1.9 Hz, 1H), 6.99 (d, J=8.1 Hz, 1H), 7.23-7.29 (m, 1H), 7.30-7.35 (m, 2H), 7.44-7.48 (m, 2H).

$^{13}$C NMR (CDCl$_3$, 125 MHz, Z-isomer): δ 13.8 (CH$_3$), 24.7 (CH$_2$), 37.8 (CH$_2$), 56.0 (CH$_3$), 59.5 (CH$_3$), 112.8 (CH), 116.6 (CH), 120.4 (CH), 125.1 (CH), 128.0 (CH), 128.4 (CH), 129.1 (CH), 134.5 (C), 138.3 (C), 143.7 (C), 145.2 (C), 149.5 (C).

Compound 15. methyl 2-((2-methoxy-2-phenylvinyl)oxy)benzoate: Starting from methyl 2-(2,2-dimethoxy-2-phenylethoxy)benzoate (13.5 g, 42.6 mmol) and KHSO$_4$ (0.06 g, 0.44 mmol), the title compound (11.4 g, 40.0 mmol) was isolated by Kugelrohr distillation (150-155° C., 3.3 Pa) as a yellow oil in 94% yield (Z/E=64:36).

$^1$H NMR (CDCl$_3$, 600 MHz, Z-isomer): δ 3.90 (s, 3H), 3.92 (s, 3H), 6.54 (s, 1H), 7.10 (t, J=7.6 Hz, 1H), 7.17 (d, J=8.4 Hz, 1H), 7.26-7.38 (m, 3H), 7.44-7.52 (m, 3H), 7.87 (dd, J=7.7, 1.6 Hz, 1H).

$^{13}$C NMR (CDCl$_3$, 150 MHz, Z-isomer): δ 52.2 (CH$_3$), 59.7 (CH$_3$), 116.2 (CH), 120.9 (C), 122.3 (CH), 125.2 (CH), 127.3 (CH), 128.1 (CH), 128.5 (CH), 131.9 (CH), 133.5 (CH), 134.2 (C), 145.1 (C), 157.0 (C), 166.3 (C).

Compound 16. methyl 3-methoxy-4-((2-methoxy-2-phenylvinyl)oxy)benzoate: Starting from methyl 4-(3,3-dimethoxy-3-phenylpropyl)-3-methoxybenzoate (22.8 g, 65.8 mmol) and KHSO$_4$ (0.09 g, 0.66 mmol), the title compound (17.2 g, 54.7 mmol) was isolated by Kugelrohr distillation (200-220° C., 2.0 Pa) as a yellow oil in 83% yield (Z/E=64:36).

$^1$H NMR (CDCl$_3$, 500 MHz, Z-isomer): δ 3.81 (s, 3H), 3.90 (s, 3H), 3.95 (s, 3H), 6.49 (s, 1H), 7.09 (d, J=8.3 Hz, 1H), 7.31-7.39 (m, 3H), 7.47-7.51 (m, 1H), 7.58-7.67 (m, 3H).

$^{13}$C NMR (CDCl$_3$, 125 MHz, Z-isomer): δ 52.1 (CH$_3$), 56.1 (CH$_3$), 59.4 (CH$_3$), 113.0 (CH), 114.7 (CH), 123.2 (CH), 124.8 (C), 125.6 (CH), 126.3 (CH), 128.3 (CH), 128.5 (CH), 133.8 (C), 145.9 (C), 149.1 (C), 150.9 (C), 166.6 (C).

Compound 17. 2-ethoxy-1-((2-methoxy-2-phenylvinyl)oxy)-4-(methoxymethyl)benzene: Starting from 1-(3,3-dimethoxy-3-phenylpropyl)-2-ethoxy-4-(methoxymethyl)benzene (20.0 g, 57.8 mmol) and KHSO$_4$ (0.08 g, 0.42 mmol), the title compound (10.4 g, 33.2 mmol) was isolated by Kugelrohr distillation (195° C., 3.3 Pa) as a yellow oil in 57% yield (Z/E=64:36).

$^1$H NMR (CDCl$_3$, 600 MHz, Z-isomer): δ 1.45 (t, J=7.0 Hz, 3H), 3.37 (s, 3H), 3.86 (s, 3H), 4.12 (q, J=7.0 Hz, 2H), 4.39 (s, 2H), 6.52 (s, 1H), 6.85 (dd, J=8.2, 1.8 Hz, 1H), 6.95 (d, J=1.8 Hz, 1H), 7.05 (d, J=8.2 Hz, 1H), 7.27 (t, J=7.5 Hz, 1H), 7.33 (t, J=7.5 Hz, 2H), 7.45-7.48 (m, 2H).

$^{13}$C NMR (CDCl$_3$, 150 MHz, Z-isomer): δ 14.9 (CH$_3$), 58.0 (CH$_3$), 59.5 (CH$_3$), 64.7 (CH$_2$), 74.4 (CH$_2$), 113.6

(CH), 116.6 (CH), 120.2 (CH), 125.0 (CH), 127.9 (CH), 128.4 (CH), 128.9 (CH), 133.6 (C), 134.4 (C), 143.6 (C), 146.9 (C), 149.2 (C).

Compound 18. 2-ethoxy-1-((2-methoxy-2-phenylvinyl)oxy)-4-methylbenzene: Starting from 1-(2,2-dimethoxy-2-phenylethoxy)-2-ethoxy-4-methylbenzene (15.8 g, 49.9 mmol) and $KHSO_4$ (0.14 g, 1.0 mmol), the title compound (11.7 g, 41.1 mmol, 82% yield) was isolated as a pale-amber oil by short-path distillation from the reaction flask (bp 168-170° C., 1.5 Pa) after the addition of 0.22 g of $Na_2CO_3$ (Z/E=51:49).

$^1$H NMR ($CD_2Cl_2$, 500 MHz, Z-isomer): δ 1.42 (t, J=7.0 Hz, 3H), 2.30 (s, 3H), 3.82 (s, 3H), 4.07 (q, J=7.0 Hz, 2H), 6.53 (s, 1H), 6.70 (d, J=8.0 Hz, 1H), 6.78 (s, 1H), 6.95 (d, J=8.0 Hz, 1H), 7.24-7.29 (m, 1H), 7.30-7.35 (m, 2H), 7.45 (d, J=7.6 Hz, 2H).

$^{13}$C NMR ($CD_2Cl_2$, 125 MHz, isomer mixture): δ 15.12 ($CH_3$), 21.16 ($CH_3$), 21.21 ($CH_3$), 57.85 ($CH_3$), 59.79 ($CH_3$), 64.95 ($CH_2$), 64.99 ($CH_2$), 115.31 (CH), 115.39 (CH), 116.00 (CH), 117.19 (CH), 121.38 (CH), 121.41 (CH), 125.12 (CH), 127.44 (CH), 127.87 (CH), 127.92 (CH), 128.21 (CH), 128.30 (CH), 128.80 (CH), 130.22 (CH), 133.31 (C), 133.94 (C), 134.08 (C), 134.95 (C), 143.33 (C), 145.51 (C), 145.73 (C), 146.30 (C), 149.16 (C), 149.22 (C).

Compound 19. 2-methoxy-1-((2-methoxy-2-(p-tolyl)vinyl)oxy)-4-propylbenzene: Starting from 1-(2,2-dimethoxy-2-(p-tolyl)ethoxy)-2-methoxy-4-propylbenzene (17.3 g, 50.3 mmol) and $KHSO_4$ (0.07 g, 0.51 mmol), the title compound (13.6 g, 43.4 mmol, 86% yield) was isolated as a pale-yellow oil by Kugelrohr distillation of the reaction mixture (185-195° C., 1.9 Pa) after the addition of 0.25 g of $Na_2CO_3$ (Z/E=55:45).

$^1$H NMR ($CDCl_3$, 500 MHz, Z-isomer): δ 0.94 (t, J=7.4 Hz, 3H), 1.62 (sextet, J=7.5 Hz, 2H), 2.33 (s, 3H), 2.55 (t, J=7.5 Hz, 2H), 3.77 (s, 3H), 3.86 (s, 3H), 6.46 (s, 1H), 6.72 (dd, J=8.0, 1.7 Hz, 1H), 6.78 (d, J=1.7 Hz, 1H), 6.96 (d, J=8.0 Hz, 1H), 7.15 (d, J=8.2 Hz, 2H), 7.34 (d, J=8.2 Hz, 2H).

$^{13}$C NMR ($CD_2Cl_2$, 125 MHz, isomer mixture): δ 13.69 ($CH_3$), 21.27 ($CH_3$), 21.38 ($CH_3$), 25.14 ($CH_2$), 25.17 ($CH_2$), 38.07 ($CH_2$), 38.09 ($CH_2$), 56.30 ($CH_3$), 56.36 ($CH_3$), 57.70 ($CH_3$), 59.67 ($CH_3$), 113.27 (CH), 113.30 (CH), 115.83 (CH), 116.70 (CH), 120.73 (CH), 120.76 (CH), 125.25 (CH), 126.96 (CH), 127.31 (CH), 129.02 (CH), 129.14 (CH), 129.49 (CH), 131.14 (C), 131.84 (C), 138.02 (C), 138.20 (C), 138.27 (C), 138.73 (C), 143.89 (C), 145.52 (C), 145.78 (C), 147.01 (C), 149.80 (C), 149.93 (C).

Compound 20. 2-methoxy-1-((2-methoxy-2-(4-methoxyphenyl)vinyl)oxy)-4-propylbenzene: Starting from 1-(2,2-dimethoxy-2-(4-methoxyphenyl)ethoxy)-2-methoxy-4-propylbenzene (17.2 g, 47.7 mmol) and $KHSO_4$ (0.13 g, 0.96 mmol), the title compound (11.8 g, 36 mmol, 75% yield) was isolated as a pale-yellow oil by Kugelrohr distillation of the reaction mixture (240° C., 2.4 Pa) after the addition of 0.2 g of $Na_2CO_3$ (Z/E=54:46).

$^1$H NMR ($CDCl_3$, 500 MHz, Z-isomer): δ 0.93 (t, J=7.4 Hz, 3H), 1.62 (sextet, J=7.5 Hz, 2H), 2.54 (t, J=7.5 Hz, 2H), 3.77 (s, 3H), 3.78 (s, 3H), 3.86 (s, 3H), 6.38 (s, 1H), 6.71 (d, J=8.2 Hz, 1H), 6.77 (d, J=1.7 Hz, 1H), 6.87 (d, J=8.7 Hz, 2H), 6.96 (d, J=8.2 Hz, 1H), 7.37 (d, J=8.7 Hz, 2H).

$^{13}$C NMR ($CD_2Cl_2$, 125 MHz, isomer mixture): δ 13.96 ($CH_3$), 25.14 ($CH_2$), 25.17 ($CH_2$), 38.06 ($CH_2$), 38.08 ($CH_2$), 55.54 ($CH_3$), 55.63 ($CH_3$), 56.28 ($CH_3$), 56.55 ($CH_3$), 57.59 ($CH_3$), 59.61 ($CH_3$), 113.24 (CH), 113.27 (CH), 113.69 (CH), 114.21 (CH), 115.70 (CH), 116.51 (CH), 120.73 (CH), 120.74 (CH), 126.16 (CH), 126.54 (C), 126.80 (CH), 127.14 (C), 128.12 (CH), 128.76 (CH), 138.11 (C), 138.58 (C), 143.94 (C), 145.58 (C), 145.80 (C), 146.86 (C), 149.78 (C), 149.88 (C), 159.72 (C), 159.89 (C).

Compound 21. cyclohexyl 2-((2-methoxy-2-phenylvinyl)oxy)benzoate: Starting from cyclohexyl 2-(2,2-dimethoxy-2-phenylethoxy)benzoate (22.7 g, 59.1 mmol) and $KHSO_4$ (0.20 g, 1.47 mmol), the title compound (4.31 g, 12.2 mmol) was isolated by silica gel flash chromatography (hexane/EtOAc 98:2) as a viscous, amber oil in 21% yield (Z/E=63:37).

$^1$H NMR ($CDCl_3$, 500 MHz, Z-isomer): δ 1.19-1.66 (m, 6H), 1.76-1.85 (m, 2H), 1.94-2.02 (m, 2H), 3.90 (s, 3H), 5.05 (m, 1H), 6.52 (s, 1H), 7.10 (t, J=7.5 Hz, 1H), 7.16 (d, J=8.3 Hz, 1H), 7.27-7.38 (m, 3H), 7.41-7.52 (m, 3H), 7.84 (dd, J=7.7, 1.7 Hz, 1H).

$^{13}$C NMR ($CDCl_3$, 125 MHz, Z-isomer): δ 23.7 ($CH_2$), 25.5 ($CH_2$), 31.6 ($CH_2$), 57.4 ($CH_3$), 73.3 (CH), 116.3 (CH), 122.0 (C), 122.3 (CH), 125.2 (CH), 127.2 (CH), 128.0 (CH), 128.5 (CH), 131.6 (CH), 133.1 (CH), 134.3 (C), 145.0 (C), 156.9 (C), 165.4 (C).

Compound 22. 1-isopropyl-2-((2-methoxy-2-phenylvinyl)oxy)-4-methylbenzene: Starting from 2-(2,2-dimethoxy-2-phenylethoxy)-1-isopropyl-4-methylbenzene (26 g, 82.7 mmol) and $KHSO_4$ (0.12 g, 0.88 mmol), the title compound (14.6 g, 51.8 mmol) was isolated by silica gel flash chromatography (hexane/EtOAc 100:0→90:10) as a pale-amber oil in 63% yield (Z/E=63:37).

$^1$H NMR ($CDCl_3$, 500 MHz, Z-isomer): δ 1.26 (d, J=6.9 Hz, 6H), 2.31 (s, 3H), 3.38 (septet, J=6.9 Hz, 1H), 3.87 (s, 3H), 6.57 (s, 1H), 6.85 (s, 1H), 6.89 (d, J=8.0 Hz, 1H), 7.16 (d, J=8.0 Hz, 1H), 7.28 (t, J=7.7 Hz, 1H), 7.35 (t, J=7.7 Hz, 2H), 7.50 (d, J=7.7 Hz, 2H).

$^{13}$C NMR ($CDCl_3$, 125 MHz, Z-isomer): δ 21.1 ($CH_3$), 22.9 ($CH_3$), 26.9 (CH), 57.7 ($CH_3$), 116.0 (CH), 123.7 (CH), 124.8 (CH), 125.4 (CH), 127.1 (CH), 128.0 (CH), 128.5 (CH), 134.6 (C), 134.8 (C), 136.8 (C), 143.7 (C), 155.0 (C).

Compound 23. (Z)-hex-3-en-1-yl 2-((2-methoxy-2-phenylvinyl)oxy)benzoate: A mixture of methyl 2-((2-methoxy-2-phenylvinyl)oxy)benzoate (Compound 15, 5.0 g, 17.6 mmol), (Z)-hex-3-en-1-ol (20.9 g, 209 mmol) and 1,8-diazabicyclo[5.4.0]undec-7-ene (DBU) (1.48 g, 8.9 mmol) was added to a round-bottomed flask (100 mL) equipped with a distillation head and nitrogen bubbler. The flask was heated at 120° C. for 20 h. The mixture was dissolved in diethyl ether and washed with water. The organic phase was dried over $Na_2SO_4$, filtered and concentrated under vacuum. The excess alcohol was removed by short-path distillation (bp 30-35° C., 13.3 Pa). The residue was subjected to silica gel flash chromatography (hexane/EtOAc 100:0→95:5) to afford 4.16 g (11.8 mmol, 67% yield) of the title compound as a pale-yellow oil (Z/E=66:34).

$^1$H NMR ($CDCl_3$, 600 MHz, Z-isomer): δ 0.95 (t, J=7.5 Hz, 3H), 2.08 (pentet, J=7.5 Hz, 2H), 2.52 (q, J=7.0 Hz, 2H), 3.90 (s, 3H), 4.32 (t, J=7.0 Hz, 2H), 5.39-5.45 (m, 1H), 5.49-5.55 (m, 1H), 6.52 (s, 1H), 7.09 (t, J=7.6 Hz, 1H), 7.17 (d, J=7.8 Hz, 1H), 7.26-7.37 (m, 3H), 7.43-7.51 (m, 3H) 7.85 (dd, J=7.7, 1.6 Hz, 1H).

$^{13}$C NMR ($CDCl_3$, 150 MHz, Z-isomer): δ 14.2 ($CH_3$), 20.6 ($CH_2$), 26.8 ($CH_2$), 59.7 ($CH_3$), 64.6 ($CH_2$), 116.2 (CH), 121.2 (C), 122.3 (CH), 123.8 (CH), 125.2 (CH), 127.3 (CH), 128.1 (CH), 128.5 (CH), 131.7 (CH), 133.4 (CH), 134.2 (CH), 134.6 (CH), 145.1 (C), 157.0 (C), 165.8 (C).

Compound 24. 3-methoxy-4-((2-methoxy-2-phenylvinyl)oxy)benzaldehyde: A solution of morpholine (3.6 g, 41.4 mmol) and anhydrous THF (250 mL) was cooled to 5° C. and 31.9 mL of a 20 wt % toluene solution of DIBALH (38 mmol) was added dropwise. The mixture was stirred for 4 h and then methyl 3-methoxy-4-((2-methoxy-2-phenylvinyl) oxy)benzoate (Compound 16, 5 g, 15.9 mmol) dissolved in THF (10 mL) was added. After stirring for 30 min, 13.3 mL of the DIBALH solution (15.9 mmol) was added dropwise over 10 min. The solution was stirred an additional 40 min and then 75 mL of 1N HCl was added slowly. After stirring for 5 min, the reaction mixture was diluted with diethyl ether (500 mL), placed in a separatory funnel and the phases allowed to separated. The aqueous layer was extracted with ether and the combined organic phases dried over $Na_2SO_4$, filtered and concentrated under vacuum. To aid purification, the remaining starting material was converted into the hexyl ester by heating a mixture of the crude product, hexanol (43.9 g, 429 mmol) and DBU (2.6 g, 17.2 mmol) at 120° C. for 15 h. The mixture was concentrated under vacuum and the remaining residue subjected to silica gel flash chromatography (hexane/$CH_2Cl_2$ 100:0→0:100) followed by Kugelrohr distillation to afford 2.0 g (7.03 mmol, 44% yield) of the title compound as a viscous, pale-yellow oil (Z/E=67:33).

$^1$H NMR ($CDCl_3$, 500 MHz, Z-isomer): δ 3.81 (s, 3H), 3.96 (s, 3H), 6.50 (s, 1H), 7.19 (d, J=8.2 Hz, 1H), 7.31-7.40 (m, 3H), 7.41-7.52 (m, 4H), 9.88 (s, 1H).

$^{13}$C NMR ($CDCl_3$, 125 MHz, Z-isomer): δ 56.1 ($CH_3$), 59.4 ($CH_3$), 110.1 (CH), 114.6 (CH), 125.6 (CH), 125.8 (CH), 126.0 (CH), 128.5 (CH), 128.6 (CH), 131.7 (C), 133.5 (C), 146.5 (C), 150.0 (C), 152.3 (C), 190.8 (C).

Compound 25. 1-((2-butoxy-2-phenylvinyl)oxy)-2-methoxy-4-propylbenzene: 1-(2,2-dimethoxy-2-phenylethoxy)-2-methoxy-4-propylbenzene (10 g, 30.2 mmol), prepared as described in the General experimental part for compounds 13 through 22, was combined with butanol (4.48 g, 60.4 mmol) and $KHSO_4$ (0.08 g, 0.60 mmol) in a round-bottomed flask equipped with a distillation head. The mixture was heated with an oil bath at 120° C. for 3 h while allowing liberated MeOH to distill from the flask. The mixture then was placed under vacuum (80 mbar) and heated at 140° C. for 2 h while allowing excess butanol to distill from the flask. The mixture was removed from the oil bath and $Na_2CO_3$ (0.25 g) was added. The reaction mixture was dissolved in diethyl ether and washed with sat. $Na_2CO_3$ and water. The organic phase was dried over $Na_2SO_4$, filtered and concentrated under vacuum. The residue was subjected to silica gel flash chromatography (hexane/EtOAc 100:0→95:5) to afford 6.94 g (20.3 mmol, 67% yield) of the title compound as a pale yellow, viscous oil (Z/E=70:30).

$^1$H NMR ($CDCl_3$, 500 MHz, Z-isomer): δ 0.93 (t, J=7.6, 3H), 0.94 (t, J=7.5 Hz, 3H), 1.47 (sextet, J=7.6 Hz, 2H), 1.63 (sextet, J=7.6 Hz, 2H), 1.72 (pentet, J=7.3 Hz, 2H), 2.55 (t, J=7.6 Hz, 2H), 3.87 (s, 3H), 4.01 (t, J=6.6 Hz, 2H), 6.50 (s, 1H), 6.70 (b d, J=8.1 Hz, 1H), 6.76 (b s, 1H), 6.98 (d, J=8.1 Hz, 1H) 7.22-7.28 (m, 1H), 7.30-7.35 (m, 2H), 7.48 (d, J=7.6 Hz, 2H).

$^{13}$C NMR ($CDCl_3$, 150 MHz, Z-isomer): δ 13.9 ($CH_3$), 19.2 ($CH_2$), 24.7 ($CH_2$), 32.2 ($CH_2$), 37.8 ($CH_2$), 56.1($CH_3$), 71.3 ($CH_2$), 113.0 (CH), 116.6 (CH), 120.5 (CH), 125.1 (CH), 127.9 (CH), 128.4 (CH), 129.2 (CH), 135.1 (C), 138.1 (C), 142.5 (C), 145.3 (C), 149.5 (C).

Compound 26. 2-methoxy-1-((2-(octyloxy)-2-phenylvinyl)oxy)-4-propylbenzene: 1-(2,2-dimethoxy-2-phenylethoxy)-2-methoxy-4-propylbenzene (6 g, 18.1 mmol), prepared as described in General experimental for compounds 13 through 22, was combined with octanol (4.73 g, 36.3 mmol) and $KHSO_4$ (0.1 g, 0.73 mmol) in a round-bottomed flask equipped with a distillation head. The mixture was heated with an oil bath at 140° C. for 2 h while allowing liberated MeOH to distill from the flask. The mixture then was placed under vacuum (3.5 kPa) and heated at 140-150° C. for 3 h while allowing excess octanol to distill from the flask. The mixture was removed from the oil bath and $Na_2CO_3$ (0.25 g) was added. The reaction mixture was dissolved in diethyl ether and washed with sat. $Na_2CO_3$ and water. The organic phase was dried over $Na_2SO_4$, filtered and concentrated under vacuum. The residue was subjected to silica gel flash chromatography (hexane/EtOAc 100:0→98:2) to afford 5.29 g (13.3 mmol, 71% yield) of the title compound as a colorless, viscous oil (Z/E=90:10).

$^1$H NMR ($CD_2Cl_2$, 600 MHz, Z-isomer): δ 0.87 (t, J=7.0, 3H), 0.94 (t, J=7.4 Hz, 3H), 1.21-1.35 (m, 8H), 1.38-1.46 (m, 2H), 1.63 (sextet, J=7.4 Hz, 2H), 1.71 (pentet, J=7.2 Hz, 2H), 2.55 (t, J=7.6 Hz, 2H), 3.86 (s, 3H), 3.95 (t, J=6.7 Hz, 2H), 6.52 (s, 1H), 6.72 (dd, J=8.1, 1.7 Hz, 1H), 6.79 (d, J=1.7 Hz, 1H), 6.96 (d, J=8.1 Hz, 1H) 7.24-7.27 (m, 1H), 7.32 (t, J=7.6 Hz, 2H), 7.46 (d, J=7.6 Hz, 2H).

$^{13}$C NMR ($CD_2Cl_2$, 150 MHz, Z-isomer): δ 14.0 ($CH_3$), 14.3 ($CH_3$), 23.1 ($CH_2$), 25.2 ($CH_2$), 26.4 ($CH_2$), 29.7 ($CH_2$), 29.8 ($CH_2$), 30.5 ($CH_2$), 32.3 ($CH_2$), 38.1 ($CH_2$), 56.3($CH_3$), 72.0 ($CH_2$), 113.4 (CH), 116.9 (CH), 120.8 (CH), 125.3 (CH), 127.9 (CH), 128.8 (CH), 130.0 (CH), 135.4 (C), 138.8 (C), 142.5 (C), 145.6 (C), 150.0 (C).

Compound 27. 1-((2-(((Z)-hex-3-en-1-yl)oxy)-2-phenylvinyl)oxy)-2-methoxy-4-propylbenzene: Compound 14 (8 g, 26.8 mmol) was combined with (Z)-3-hexen-1-ol (8.1 g, 80.9 mmol) and $KHSO_4$ (0.23 g, 1.7 mmol) in a 35 mL, round-bottomed flask equipped with a distillation head. The mixture was heated with an oil bath at 140° C. for 1.5 h while allowing liberated MeOH to distill from the flask. The mixture then was placed under vacuum (8 kPa) and heated at 140-150° C. for 4 h while allowing excess (Z)-3-hexen-1-ol to distill from the flask. The mixture was removed from the oil bath and $Na_2CO_3$ (0.25 g) was added. The reaction mixture was filtered through a bed of silica gel and concentrated under vacuum. $KHSO_4$ (0.2 g) was added, and using a Kugelrohr distillation apparatus, the mixture was heated an additional 1.5 h at 150° C. (2 kPa). The crude product was subjected to silica gel flash chromatography (hexane/EtOAc 100:0→97.5:2.5) to afford 5.14 g (14.0 mmol, 52% yield) of the title compound as an amber oil (Z/E=71:29).

$^1$H NMR ($CD_2Cl_2$, 500 MHz, Z-isomer): δ 0.93 (t, J=7.5 Hz, 3H), 0.94 (t, J=7.4 Hz, 3H), 1.62 (sextet, J=7.5 Hz, 2H), 2.05 (pentet, J=7.4 Hz, 2H), 2.49 (t, J=7.0 Hz, 2H), 2.55 (t, J=7.5 Hz, 2H), 3.86 (s, 3H), 3.98 (t, J=7.0 Hz, 2H), 5.39-5.55 (m, 2H), 6.54 (s, 1H), 6.72 (dd, J=8.1, 1.9 Hz, 1H), 6.79 (d, J=1.9 Hz, 1H), 6.97 (d, J=8.1 Hz, 1H), 7.23-7.28 (m, 1H), 7.32 (t, J=7.9 Hz, 2H), 7.47 (d, J=7.9 Hz, 2H).

$^{13}$C NMR ($CD_2Cl_2$, 125 MHz, Z-isomer): δ 14.0 ($CH_3$), 14.4 ($CH_3$), 21.0 ($CH_2$), 25.1 ($CH_2$), 28.6 ($CH_2$), 38.1 ($CH_2$), 56.3 ($CH_3$), 71.5 ($CH_2$), 113.4 (CH), 116.9 (CH), 120.8 (CH), 125.1 (CH), 125.3 (CH), 127.9 (CH), 128.8 (CH), 130.1 (CH), 134.2 (CH), 135.3 (C), 138.9 (C), 142.2 (C), 145.5 (C), 150.0 (C).

Compound 28. 2-methoxy-1-((2-phenethoxy-2-phenylvinyl)oxy)-4-propylbenzene: Compound 14 (6.67 g, 22.4 mmol) was combined with 2-phenylethanol (5.47 g, 44.7 mmol) and $KHSO_4$ (0.15 g, 1.1 mmol) in a 25 mL, round-bottomed flask equipped with a distillation head. The mixture was heated with an oil bath at 150° C. for 1.5 h while allowing liberated MeOH to distill from the flask. The mixture then was placed under vacuum (2 kPa) and heated at 150° C. for 4 h while allowing excess 2-phenylethanol to distill from the flask. Additional $KHSO_4$ (0.12 g, 0.88 mmol) was added and the mixture heated an additional 2 h. The mixture was removed from the oil bath and $Na_2CO_3$ (0.25 g) was added. The crude product was subjected to silica gel flash chromatography (hexane/EtOAc 100:0→97.5:2.5) to afford 6.62 g (17.0 mmol, 76% yield) of the title compound as a pale-amber, viscous oil (Z/E=70:30).

$^1$H NMR (CD$_2$Cl$_2$, 600 MHz, Z-isomer): δ 0.94 (t, J=7.4 Hz, 3H), 1.63 (sextet, J=7.4 Hz, 2H), 2.55 (t, J=7.5 Hz, 2H), 3.05 (t, J=7.2 Hz, 2H), 3.85 (s, 3H), 4.20 (t, J=7.2 Hz, 2H), 6.55 (s, 1H), 6.72 (dd, J=8.1, 1.8 Hz, 1H), 6.79 (d, J=1.8 Hz, 1H), 6.97 (d, J=8.1 Hz, 1H), 7.17-7.36 (m, 10H).

$^{13}$C NMR (CD$_2$Cl$_2$, 150 MHz, Z-isomer): δ 14.0 (CH$_3$), 25.1 (CH$_2$), 36.9 (CH$_2$), 38.1 (CH$_2$), 56.3 (CH$_3$), 72.6 (CH$_2$), 113.3 (CH), 116.9 (CH), 120.8 (CH), 125.2 (CH), 126.6 (CH), 127.9 (CH), 128.7 (CH), 129.5 (CH), 130.1 (CH), 135.1 (C), 138.9 (C), 139.2 (C), 142.2 (C), 145.4 (C), 150.0 (C).

Compound 29. 2-ethoxy-1-((2-ethoxy-2-phenylvinyl)oxy)-4-methylbenzene: A mixture of 2-(2-ethoxy-4-methylphenoxy)-1-phenylethan-1-one (10 g, 37 mmol; prepared as described for compound 18) was converted to the diethyl acetal by mixing with triethyl orthoformate (7 equiv.), ethanol (200 ml) and p-toluene sulfonic acid (0.03 equiv.) and heating the solution at 80° C. for 4 h. Solid Na$_2$CO$_3$ (1.0 g) was added and the mixture was concentrated under vacuum. The remaining residue was dissolved in diethyl ether and washed with water, sat. NH$_4$Cl and water. The organic phase was dried over Na$_2$SO$_4$, filtered and concentrated under vacuum. The resulting diethyl acetal was combined with KHSO$_4$ (0.02 equiv) in a round-bottomed flask equipped with a distillation head. The mixture was placed under vacuum (1.5 kPa) and then heated with an oil bath at 140° C. for 3 h. The mixture was removed from the oil bath and Na$_2$CO$_3$ (0.2 g) was added. The reaction mixture was dissolved in diethyl ether and washed with sat. Na$_2$CO$_3$ and water. The organic phase was dried over Na$_2$SO$_4$, filtered and concentrated under vacuum. The resulting enol ether was purified by silica gel flash chromatography (hexane/CH$_2$Cl$_2$ 90:10→60:40) to afford 2.19 g (7.34 mmol, 20% yield) of the title compound as a pale yellow oil (Z/E=62:38).

$^1$H NMR (CD$_2$Cl$_2$, 600 MHz, Z-isomer): δ 1.34 (t, J=7.1 Hz, 3H), 1.42 (t, J=7.0 Hz, 3H), 2.30 (s, 3H), 4.04 (q, J=7.0 Hz, 2H), 4.05 (q, J=7.1 Hz, 2H), 6.56 (s, 1H), 6.70 (d, J=8.1 Hz, 1H), 6.78 (s, 1H), 6.95 (d, J=8.1 Hz, 1H), 7.23-7.27 (m, 1H), 7.29-7.36 (m, 2H), 7.47 (d, J=7.7 Hz, 2H).

$^{13}$C NMR (CD$_2$Cl$_2$, 150 MHz, Z-isomer): δ 15.1 (CH$_3$), 15.7 (CH$_3$), 21.2 (CH$_3$), 65.0 (CH$_2$), 67.5 (CH$_2$), 115.4 (CH), 117.2 (CH), 121.4 (CH), 125.1 (CH), 127.8 (CH), 128.8 (CH), 130.5 (CH), 133.9 (C), 135.4 (C), 141.9 (C), 145.6 (C), 149.3 (C).

Compound 30. methyl 4-((2-(hexyloxy)-2-phenylvinyl)oxy)-3-methoxybenzoate: Compound 16 (18.5 g, 58.9 mmol) was combined with 1-hexanol (24 g, 235.4 mmol) and KHSO$_4$ (0.32 g, 2.35 mmol) in a round-bottomed flask equipped with a distillation head. The mixture was heated with an oil bath at 140° C. for 1 h while allowing liberated MeOH to distill from the flask. The mixture was placed under vacuum, which was gradually reduced from 50 to 1.1 kPa and heated at 150° C. for 2 h while distilling 1-hexanol from the flask. The mixture was removed from the oil bath and Na$_2$CO$_3$ (0.5 g) was added. The reaction mixture was dissolved in dichloromethane and washed with sat. Na$_2$CO$_3$ and water. The organic phase was dried over MgSO$_4$, filtered and concentrated under vacuum. The resulting residue was subjected to silica gel flash chromatography (hexane/EtOAc 100:0→91:9) to afford 14.4 g (37.5 mmol, 64% yield) of the title compound as a pale-amber oil (Z/E=67:33).

$^1$H NMR (CD$_2$Cl$_2$, 600 MHz, Z-isomer): δ 0.86 (t, J=6.8 Hz, 3H), 1.21-1.32 (m, 4H), 1.32-1.43 (m, 2H), 1.68 (pentet, J=7.4 Hz, 2H), 3.67 (s, 3H), 3.93 (s, 3H), 3.95 (t, J=6.6 Hz, 2H), 6.56 (s, 1H), 7.09 (d, J=8.3 Hz, 1H), 7.26-7.39 (m, 3H), 7.50 (d, J=7.5 Hz, 2H), 7.57-7.65 (m, 2H).

$^{13}$C NMR (CD$_2$Cl$_2$, 150 MHz, Z-isomer): δ 14.2 (CH$_3$), 23.0 (CH$_2$), 26.0 (CH$_2$), 30.4 (CH$_2$), 32.0 (CH$_2$), 52.3 (CH$_3$), 56.5 (CH$_3$), 72.1 (CH$_2$), 113.5 (CH), 115.0 (CH), 123.4 (CH), 125.2 (C), 125.8 (CH), 127.2 (CH), 128.5 (CH), 128.8 (CH), 134.8 (C), 144.9 (C), 149.6 (C), 151.3 (C), 166.8 (C).

Compound 31. (4-((2-(hexyloxy)-2-phenylvinyl)oxy)-3-methoxyphenyl)methanol: A 20 wt % toluene solution of DIBALH (68 mL, 81.2 mmol) was added slowly to a solution of compound 30 (7.8 g, 20.3 mmol) in anhydrous THF (250 mL) cooled at 0° C. The mixture was warmed to 25° C. and stirred for 2 h. After cooling again at 0° C., a 40 wt % aqueous solution of Rochelle's salt (sodium potassium tartrate) was added over 15 min. The mixture was allowed to warm to room temperature and diluted with diethyl ether (100 mL) and water (50 mL). The phases were separated and the aqueous phase was extracted three times with diethyl ether. The organic phases were combined and dried over MgSO$_4$, filtered and concentrated under vacuum to afford 6.9 g (19.4 mmol, 96% yield) of the title compound as a pale-yellow, viscous oil (Z/E=69:31).

$^1$H NMR (CD$_2$Cl$_2$, 600 MHz, Z-isomer): δ 0.87 (t, J=7.0 Hz, 3H), 1.25-1.37 (m, 4H), 1.38-1.49 (m, 2H), 1.68-1.79 (m, 2H), 2.10 (b s, 1H), 3.87 (s, 3H), 3.95 (t, J=6.8 Hz, 2H), 4.60 (s, 2H), 6.53 (s, 1H), 6.87 (dd, J=8.1, 1.9 Hz, 1H), 6.98 (d, J=1.9 Hz, 1H), 7.03 (d, J=8.3 Hz, 1H), 7.24-7.29 (m, 1H), 7.33 (t, J=7.6 Hz, 2H), 7.47 (d, J=7.6 Hz, 2H).

$^{13}$C NMR (CD$_2$Cl$_2$, 150 MHz, Z-isomer): δ 14.2 (CH$_3$), 23.0 (CH$_2$), 26.0 (CH$_2$), 30.4 (CH$_2$), 32.9 (CH$_2$), 56.3 (CH$_3$), 65.1 (CH$_2$), 72.1 (CH$_2$), 111.8 (CH), 116.6 (CH), 119.5 (CH), 125.4 (CH), 128.1 (CH), 128.8 (CH), 129.3 (CH), 135.2 (C), 137.1 (C), 143.1 (C), 146.8 (C), 150.2 (C).

Compound 32. 4-((2-(hexyloxy)-2-phenylvinyl)oxy)-3-methoxybenzaldehyde: A solution of compound 31 (6.0 g, 16.8 mmol) and pyridinium chlorochromate (5.44 g, 25.2 mmol) in 50 mL of dichloromethane was heated at reflux for 6 h. After diluting with diethyl ether, the mixture was filtered through a layered bed of Celite® and silica gel. After removing the solvent under vacuum, the crude product was subjected to silica gel flash chromatography (hexane/EtOAc 100:0→90:10) to afford 2.81 g (7.9 mmol, 47% yield) of the title compound as a yellow oil (Z/E=69:31).

$^1$H NMR (CD$_2$Cl$_2$, 500 MHz, Z-isomer): δ 0.86 (t, J=6.7 Hz, 3H), 1.21-1.32 (m, 4H), 1.32-1.44 (m, 2H), 1.68 (pentet, J=7.3 Hz, 2H), 3.95 (s, 3H), 3.95 (t, J=6.5 Hz, 2H), 6.58 (s, 1H), 7.19 (d, J=7.9 Hz, 1H), 7.31-7.39 (m, 3H), 7.42-7.47 (m, 2H), 7.52 (d, J=7.8 Hz, 2H), 9.86 (s, 1H).

$^{13}$C NMR (CD$_2$Cl$_2$, 125 MHz, Z-isomer): δ 14.2 (CH$_3$), 23.0 (CH$_2$), 26.0 (CH$_2$), 30.1 (CH$_2$), 32.0 (CH$_2$), 56.4 (CH$_3$), 72.1 (CH$_2$), 110.6 (CH), 114.9 (CH), 125.9 (CH), 126.0 (C), 126.6 (CH), 128.7 (CH), 128.9 (CH), 132.2 (C), 134.6 (C), 145.5 (C), 150.5 (C), 152.6 (C), 191.0 (C).

Compound 33. methyl 2-((2-(((Z)-hex-3-en-1-yl)oxy)-2-phenylvinyl)oxy)benzoate: Compound 15 (9.97 g, 35.1 mmol) was combined with (Z)-hex-3-en-1-ol (21 g, 210 mmol) and KHSO$_4$ (0.24 g, 1.76 mmol) in a round-bottomed flask equipped with a distillation head. The mixture was placed under vacuum (20 kPa) and heated with an oil bath at 140° C. for 3 h while allowing liberated MeOH and (Z)-hex-3-en-1-ol to distill from the flask. Additional KHSO$_4$ (0.24 g, 1.76 mmol) was added, the vacuum was reduced to 2 kPa, and the mixture was heated another 2 h at 140° C. The reaction mixture was dissolved in ethyl acetate, filtered through a bed of silica gel and concentrated under vacuum. KHSO$_4$ (0.24 g) was added and the mixture was heated an additional hour at 150° C. under vacuum (2 kPa), using a Kugelrohr distillation apparatus. The crude product was subjected to silica gel flash chromatography (hexane/EtOAc 100:0→95.5:4.5) to afford 8.54 g (24.2 mmol, 69% yield) of the title compound as a pale-yellow oil (Z/E=68:32).

$^1$H NMR (CD$_2$Cl$_2$, 500 MHz, Z-isomer): δ 0.92 (t, J=7.5 Hz, 3H), 2.05 (pentet, J=7.4 Hz, 2H), 2.48 (q, J=6.9 Hz, 2H), 3.88 (s, 3H), 4.06 (t, J=6.9 Hz, 2H), 5.36-5.58 (m, 2H), 6.58 (s, 1H), 7.10 (t, J=7.5 Hz, 1H), 7.17 (d, J=8.4 Hz, 1H), 7.26-7.39 (m, 3H), 7.45-7.50 (m, 1H), 7.52 (d, J=8.0 Hz, 2H), 7.79-7.81 (m, 1H).

$^{13}$C NMR (CD$_2$Cl$_2$, 125 MHz, Z-isomer): δ 14.4 (CH$_3$), 21.0 (CH$_2$), 28.6 (CH$_2$), 52.4 (CH$_2$), 71.7 (CH$_2$), 116.4 (CH), 121.4 (C), 122.6 (CH), 125.0 (CH), 125.6 (CH), 127.0 (CH), 128.4 (CH), 128.8 (CH), 132.0 (CH), 133.8 (CH), 134.3 (CH), 135.0 (C), 144.3 (C), 157.2 (C), 166.5 (C).

Compound 34. (Z)-hex-3-en-1-yl 2-((2-(((Z)-hex-3-en-1-yl)oxy)-2-phenylvinyl)oxy)benzoate: A mixture of methyl 2-((2-(((Z)-hex-3-en-1-yl)oxy)-2-phenylvinyl)oxy)benzoate (Compound 33, 5.0 g, 14.2 mmol), (Z)-hex-3-en-1-ol (26.4 g, 264 mmol) and DBU (1.34 g, 8.1 mmol) was added to a round-bottomed flask (100 mL) equipped with a distillation head. The mixture was heated at 160° C. under vacuum (30 kPa) for 26 h while allowing MeOH and (Z)-hex-3-en-1-ol to distill from the flask. The mixture was dissolved in ethyl acetate and washed with water. The organic phase was dried over MgSO$_4$, filtered and concentrated. The residue was subjected to silica gel flash chromatography (hexane/EtOAc 90:10→85:15) to afford 3.59 g (8.5 mmol, 60% yield) of the title compound as a colorless oil (Z/E=69:31).

$^1$H NMR (CD$_2$Cl$_2$, 150 MHz, Z-isomer): δ 0.92 (t, J=7.4 Hz, 3H), 0.95 (t, J=7.6 Hz, 3H), 2.04 (pentet, J=7.3 Hz, 2H), 2.08 (pentet, J=7.5 Hz, 2H), 2.47 (q, J=7.2 Hz, 2H), 2.51 (q, J=7.3 Hz, 2H), 4.05 (t, J=6.9 Hz, 2H), 4.29 (t, J=6.9 Hz, 2H), 5.33-5.57 (m, 4H), 6.57 (s, 1H), 7.10 (t, J=7.5 Hz, 1H), 7.17 (d, J=8.3 Hz, 1H), 7.24-7.38 (m, 3H), 7.44-7.50 (m, 1H), 7.52 (d, J=8.0 Hz, 2H), 7.79-7.81 (m, 1H).

$^{13}$C NMR (CD$_2$Cl$_2$, 600 MHz, Z-isomer): δ 14.4 (CH$_3$), 21.0 (CH$_2$), 27.2 (CH$_2$), 28.6 (CH$_2$), 64.9 (CH$_2$), 71.7 (CH$_2$), 116.5 (CH), 121.8 (C), 122.6 (CH), 124.2 (CH), 125.1 (CH), 125.6 (CH), 127.1 (CH), 128.4 (CH), 128.8 (CH), 131.9 (CH), 133.7 (CH), 134.2 (CH), 134.8 (CH), 135.0 (C), 144.3 (C), 157.2 (C), 165.9 (C).

Compound 35. (3-methoxy-4-((2-methoxy-2-phenylvinyl)oxy)phenyl)methanol: A 20 wt % toluene solution of DIBALH (108.8 mL, 129.8 mmol) was added slowly to a solution of compound 16 (10.2 g, 32.4 mmol) in anhydrous THF (250 mL) cooled at 0° C. The mixture was warmed to 25° C. and stirred for 2 h. After cooling again at 0° C., a 40 wt % aqueous solution of Rochelle's salt (sodium potassium tartrate) was added over 15 min. The mixture was allowed to warm to room temperature and diluted with diethyl ether (100 mL) and water (50 mL). The phases were separated and the aqueous phase was extracted three times with diethyl ether. The organic phases were combined and dried over MgSO$_4$, filtered and concentrated under vacuum. The residue was subjected to silica gel flash chromatography (hexane/EtOAc 100:0→70:30) to afford 4.0 g (14.0 mmol, 43% yield) of the title compound as a pale-yellow, viscous oil (Z/E=70:30).

$^1$H NMR (CDCl$_3$, 500 MHz, Z-isomer): δ 1.70 (b s, 1H), 3.83 (s, 3H), 3.91 (s, 3H), 4.65 (s, 2H), 6.49 (s, 1H), 6.88 (dd, J=8.2, 1.9 Hz, 1H), 7.00 (d, J=1.9 Hz, 1H), 7.06 (d, J=8.2 Hz, 1H), 7.27-7.38 (m, 3H), 7.47 (b d, J=8.3 Hz, 2H).

$^{13}$C NMR (CDCl$_3$, 125 MHz, Z-isomer): δ 56.0 (CH$_3$), 59.5 (CH$_3$), 65.2 (CH$_2$), 111.3 (CH), 116.3 (CH), 119.2 (CH), 125.3 (CH), 127.1 (CH), 128.3 (CH), 128.5 (CH), 134.2 (C), 136.2 (C), 143.1 (C), 146.8 (C), 150.2 (C).

Example 3

Headspace Analysis from Fabric Softener Application Comprising Invention's Compounds of Formula (I)

A model liquid fabric softener was prepared by mixing a TEA-esterquat (Stepantex® VL 90A), 12.3 wt %, 10% aqueous calcium chloride, 0.4 wt %, Proxcel GXL, 0.04 wt % and deionized water, 87.2 wt %. The enol ethers (0.075 mmol) were weighed into a vial and dissolved in 0.03 g of acetone. Liquid fabric softener (4.5 g) was added to the vial and the mixture shaken by hand to mix. Reference samples were prepared in the same manner using 0.075 mmol of each released volatile. The fabric softener samples were rinsed with deionized water into a 3 L beaker and the beaker was filled to a total volume of 1.5 L. Three, 5-g cotton swatches (ca. 12.5×12.5 cm, weight 270 g/m$^2$, item 403 from Testfabrics, West Pittston, PA) were added to the beaker and agitated by hand for 3 min. After an additional 2 min of standing, the swatches were removed and excess water squeezed out by hand. The cloths were hung to dry for 1 day or 3 days at rt. Two of the three swatches were placed inside a thermostatted (35° C.), headspace sampling cell (about 160 mL volume). Using an air-sampling pump, a constant flow of air (200 mL/min) was drawn through the sampling cell and then through a cartridge containing 100 mg of Tenax®. Prior to entering the sample cell, the air was drawn through a plug of active charcoal and then through a saturated NaCl solution to maintain a constant relative humidity of 75%. For each swatch, headspace samples were collected over a 2-hour period as 4, 30-minute samples. The average headspace concentration for the released perfumery ingredients for the two swatches over the 2 hours is reported.

The cartridges were thermally desorbed with a Perkin Elmer TurboMatrix 650 thermal desorber coupled to an Agilent 6890 gas chromatograph equipped with an Agilent 5975C mass spectrometer and a Varian VF-1 ms capillary column (30 m, i.d. 0.25 mm, film 0.25 μm). The desorber parameters were: valve temperature 250° C., transfer line 240° C., purge time 1 min, desorption temperature 240° C., desorption time 5 min, desorption flow 1 mL/min, trap −30° C. to 240° C. at 40° C./sec, trap hold time 5 min, outlet split 95 mL/min, column flow 1 mL/min. The GC oven temperature profile was 60° C. (1 min) to 210° C. at 20° C./min then ramped to 250° C. (2 min). The amount of each fragrance volatile collected (reported as ng/L of air) was determined using external standard calibrations of the respective chemicals. At least five acetone solutions were prepared with concentrations of the analytes ranging from 0.05 g/L to 5 g/L. The solutions were injected (0.2 μL) onto Tenax® cartridges and desorbed as described above. Each solution was analyzed in triplicate. Calibration curves were forced through the origin.

Dynamic headspace concentrations (ng/L) of perfumery raw materials obtained from line-dried cotton treated with fabric softener containing enol ether profragrances compared to their respective references (average conc. over 2-h of sampling headspace).

|  |  | Line dried for 1 day | | Line dried for 3 days | |
|---|---|---|---|---|---|
|  |  | profragrance | reference | profragrance | reference |
| Cpd. 1 | acetophenone | 104 | 3 | 126 | 4 |
|  | eugenol | 136 | 50 | 234 | 24 |
| Cpd. 3 | acetophenone | 371 | <1 | 63 | 7 |
|  | dihydroeugenol | 317 | 81 | 95 | 41 |
| Cpd. 5 | 2-undecanone | 273 | 8 | 298 | 14 |
|  | eugenol | 293 | 21 | 254 | 12 |
| Cpd. 6 | 2-undecanone | 228 | 6 | 181 | 5 |
|  | dihydroeugenol | 216 | 22 | 125 | 16 |
| Cpd. 13 | methyl benzoate | 107 | 1 | 120 | 2 |
|  | eugenol | 120 | 2 | 75 | 22 |
| Cpd. 14 | methyl benzoate | 77 | <1 | 74 | not detected |
|  | dihydroeugenol | 104 | 13 | 81 | 15 |
| Cpd. 17 | methyl benzoate | 51 | <1 | 274 | <1 |
|  | 2-ethoxy-4-methylphenol | 161 | <1 | 638 | 2 |
| Cpd. 20 | methyl 4-methoxybenzoate | 26 | <1 | not determined | not determined |
|  | dihydroeugenol | 90 | 7 | not determined | not determined |
| Cpd. 25 | butyl benzoate | 196 | 5 | 167 | <1 |
|  | dihydroeugenol | 288 | 45 | 240 | 4 |

These data indicate that, when applied to cotton fabric from a fabric softener application, the compounds of formula (I) release considerably more perfumery ingredients (ketones and phenols) than the corresponding reference samples. This demonstrates that the compounds of the invention produced the desired slow-release effect.

Example 4

Olfactive Evaluation with a Leave-on Hair Conditioner Comprising Invention's Compounds of Formula (I)

A model rinse-off hair conditioner was prepared with following composition (weight %):

| Deionized water | 95.50% |
|---|---|
| Salcare SC 91 (origin: BASF) | 1.00% |
| Aculyn ™ 46 (origin: Dow) | 1.00% |
| Wacker-Belsil ® DMS 6038 (origin: Wacker) | 0.50% |
| Phenonip ™ (origin: Clariant) | 0.50% |
| Mirasil ® ADM-E (origin: Elkem) | 1.50% |

A 25% enol ether solution in isopropyl myrisate or a 25% enol ether solution in acetone was dispersed in a leave-on hair conditioner to provide samples containing 0.15 wt % or 0.25 wt % of the precursor, respectively. Reference samples containing an equimolar level of the expected ketone and phenol were prepared in the same way. The samples were left macerating at room temperature for one day. The hair swatches (10 g) were rinsed under warm tap water (37° C.) for 30 s then gently combed to straighten the hair. The hair conditioner samples (1 g) were each applied to a swatch and massaged into the hair to disperse thoroughly. The swatches were hung and allowed to dry at room temperature. They were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in the below table.

| Tested molecule (wt % in conditioner) | Mean Odor Intensity (# of panelists) | |
|---|---|---|
| Reference materials | 6 hours | 24 hours |
| Compound 4 (0.25%) | 4.29 (17) | 4.71 (14) |
| acetophenone, raspberry ketone | 2.35 (17) | 2.64 (14) |
| Compound 1 (0.25%) | 4.67 (12) | 4.58 (13) |
| eugenol, acetophenone | 3.5 (12) | 2.92 (13) |
| Compound 4 (0.15%) | 3.63 (15) | 3.33 (15) |
| acetophenone, raspberry ketone | 2.13 (15) | 2.07 (15) |
| Compound 1 (0.15%) | 4.37 (19) | 4.63 (15) |
| eugenol, acetophenone | 2.68 (19) | 1.33 (15) |
| Compound 13 (0.15%) | 4.28 (25) | 4.54 (22) |
| eugenol, methyl benzoate | 2.24 (25) | 1.95 (22) |

These data show that the compounds of formula (I) produced a higher odor intensity on hair than the corresponding reference samples at both 6 h and 24 h after application from a leave-on hair conditioner. This demonstrates that the compounds of the invention produced the desired slow-release effect.

Example 5

Olfactive Evaluation with a Rinse-Off Hair Conditioner Comprising Invention's Compounds of Formula (I)

A model rinse-off hair conditioner was prepared with following composition (weight %)

| Deionized water | 92.54% |
|---|---|
| Chlorhexidine dihydrochloride | 0.05% |
| Natrosol ® 250 H (origin: Hercules) | 1.00% |
| Dehyquart ® C 4046 (origin: Cognis) | 0.20% |
| Mirasil ® ADM-E (origin: Rhodia) | 1.20% |
| Genamin ® KDM (origin: Clariant) | 1.00% |
| Crodamol ® SS (origin: Croda) | 0.50% |
| Crodacol ® C90 (origin: Croda) | 3.01% |
| Myristyl alcohol (origin: Aldrich) | 0.20% |
| Nipagin ® M (origin: Nipa) | 0.30% |

A 25% enol ether solution in isopropyl myrisate was dispersed in a rinse-off hair condition at 1% to provide a conditioner containing 0.25 or 0.15 wt % of the precursor. A reference sample containing an equimolar level of the expected ketone and phenol was prepared in the same way. The samples were left macerating at room temperature for one day. Hair swatches (10 g) were wetted with warm tap water (about 37° C.) and washed with an unperfumed milky shampoo. The shampoo (1 mL) was applied with a syringe along the length of each hair swatch. The swatches were massaged with fingertips for 30 s to distribute the shampoo and develop a good lather. They were rinsed with warm tap water for 30 s and the excess water gently squeezed out. The rinse-off conditioner (1.0 g) was applied along the hair swatch and gently massaged into the hair for 1 min. The swatch was then dipped in a 2-L beaker of warm tap water and moved up and down three times and then side-to-side three times. It then was rinse for 30 s with tap water while detangling the hair with fingertips. After gently squeezing out excess water, the swatches were hung and allowed to dry at room temperature. The swatches were olfactively evaluated by a panel for odor intensity after 24 h. Panelists were asked to rate the perceived odor intensity on a scale ranging from 1 (imperceptible) to 7 (very intense). The data obtained from the panel evaluation are summarized in the below table.

| Tested molecule (wt % in conditioner) Reference materials | Mean Odor Intensity at 24 hours (# of panelists) |
|---|---|
| Compound 1 (0.25%) | 4.13 (31) |
| Eugenol, acetophenone | 2.37 (31) |
| Compound 4 (0.25%) | 3.69 (13) |
| Acetophenone, raspberry ketone | 1.85 (13) |
| Compound 4 (0.15%) | 4.32 (17) |
| Acetophenone, raspberry ketone | 1.94 (17) |
| Compound 13 (0.25%) | 3.38 (26) |
| Eugenol, methyl benzoate | 2.42 (26) |
| Compound 13 (0.15%) | 3.05 (20) |
| Eugenol, methyl benzoate | 1.98 (20) |

These data show that the compounds of formula (I) produced a higher odor intensity on hair than the corresponding reference samples after application from a rinse-off hair conditioner. This demonstrates that the compounds of the invention produced the desired slow-release effect.

Example 6

Olfactive Evaluation with an Antiperspirant/Deodorant Stick Comprising Invention's Compounds of Formula (I)

A model deodorant was prepared in a generally known manner with following composition (weight %)

| Dow Corning 345 Fluid | 55.00% |
| Lanette ® 18 (origin: BASF) | 21.00% |
| Tegosoft ® PBE (origin: Evonik) | 2.00% |
| Cutina ® HR (origin: BASF) | 1.00% |
| Summit ® AZP-908 (origin: SummitReheis) | 20.00% |

A sample containing 0.15 wt % of an enol ether profragrance was prepared by dispersing a 15:20 mixture of the enol ether and isopropyl myrisate in the molten antiperspirant composition. A reference sample containing an equimolar level of the expected ketone and formate ester was prepared in the same way. The molten samples were poured into deodorant stick molds and left macerating at room temperature for one day. An amount of 0.25 g of each sample was spread evenly on paper blotters of 4.5 cm×12 cm. The blotters were stored under ambient conditions for 24 h. Panelists were asked to rate the perceived odor intensity on a scale ranging from 1 (imperceptible) to 7 (very intense). The data obtained from the panel evaluations are summarized in the below table.

| Tested molecule (wt % in AP/Deo stick) Reference materials | Mean Odor Intensity at 24 hours (# of panelists) |
|---|---|
| Compound 1 (0.15%) | 3.86 (25) |
| Eugenol, acetophenone | 2.00 (25) |
| Compound 13 (0.15%) | 3.17 (18) |
| Eugenol, methyl benzoate | 2.28 (18) |

These data show that the compounds of formula (I) produced higher odor intensities on blotters than the corresponding reference samples after application from an antiperspirant stick. This demonstrates that the compounds of the invention produced the desired slow-release effect.

The invention claimed is:
1. A method to release, from a precursor compound, compounds selected from the group consisting of
a) a carbonyl compound of formula

(II)

wherein when $R^2$ represents a $OR^{2'}$ wherein $R^{2'}$ represents a $C_{1-12}$ alkyl group, a $C_{3-12}$ alkenyl group, a phenethyl group, or a benzyl group, then $R^1$ is a phenyl group optionally substituted by one or two $R^{1'}$ group wherein $R^{1'}$, simultaneously or independently, represents a hydroxyl group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent RT, when taken together, represent a —O—$(CH_2)_m$—O— wherein m is 1 or 2 or form a $C_{5-6}$ saturated or unsaturated ring;
when $R^2$ represents a $C_{1-6}$ alkyl or a $C_{6-10}$ aryl group each optionally substituted by a hydroxyl group, a $C_{1-3}$ alkyl group, a $C_{1-3}$ alkoxy group, then $R^1$ represents a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group; or
$R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula

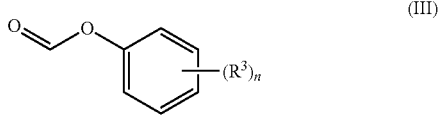

wherein n represents an integer between 1 and 5;
$R^3$, simultaneously or independently, represents at least one substituent of the aromatic ring and is a $C_{1-6}$ alkyl group optionally substituted by a hydroxy, $C_{1-6}$ alkoxy or oxo group; a $C_{4-7}$ oxacycloalkyl or oxacycloalkenyl group optionally substituted with a $C_{1-3}$ alkyl or a methylene group; a $C_{2-6}$ alkenyl group; a $C_{1-6}$ alkoxy group; or a $R^bOCO$ group wherein $R^b$ is a hydrogen atom, a $C_{1-7}$ alkyl group, a $C_{2-7}$ alkenyl group, a $C_{3-7}$ cycloalkyl group, a benzyl group or a phenethyl group; and c) an alcohol of formula

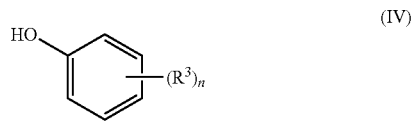

wherein $R^3$ has the same meaning as defined above;
wherein the precursor compound comprises a compound of formula (I)

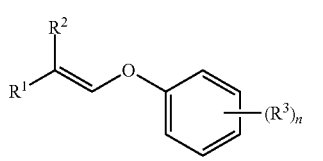

in the form of any one of its stereoisomers or a mixture thereof, and wherein n, $R^1$, $R^2$ and $R^3$ have the same meaning as defined above; the method comprising exposing the precursor compound of formula (I) to an environment wherein the compound is oxidized.

2. The method according to claim 1, wherein n is 1, 2 or 3.

3. The method according to claim 1, wherein $R^2$ represents a $C_{1-3}$ alkyl group and $R^1$ represents a $C_{6-10}$ aryl or $C_{1-10}$ alkyl group optionally substituted with a phenyl, $C_{5-7}$ cycloalkyl and/or $C_{5-7}$ cycloalkenyl group, each optionally substituted with one or more of a $C_{1-4}$ alkyl and/or $C_{1-4}$ alkoxy group.

4. The method according to claim 1, wherein $R^2$ represents a $OR^{2'}$ wherein $R^{2'}$ represents a $C_{1-6}$ alkyl group, phenethyl group or a benzyl group and $R^1$ is a phenyl group optionally substituted by one or two $R^{1'}$ group wherein $R^{1'}$, simultaneously or independently, represents a hydroxyl group, a $C_{1-3}$ alkyl group, a $C_{1-3}$ alkoxy group.

5. The method according to claim 1, wherein $R^3$ represents a $C_{1-6}$ alkyl group optionally substituted by a hydroxy, a $C_{1-2}$ alkoxy or an oxo group; a $C_{2-6}$ alkenyl group; a $C_{1-3}$ alkoxy group; or a $R^bOCO$ group wherein $R^b$ is a hydrogen atom, a $C_{1-7}$ alkyl, a $C_{2-7}$ alkenyl or a cyclohexyl group.

6. The method according to claim 1, wherein at least one of the compounds of formula (II), (III) or (IV) is a perfuming ingredient.

7. The method according to claim 1, wherein at least two of the compounds of formula (II), (III) or (IV) are a perfuming ingredient.

8. The method according to claim 1, wherein the environment wherein the compound is oxidized is air.

9. A method to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined in claim 1.

10. A method for intensifying or prolonging the diffusion effect of the characteristic fragrance of at least one carbonyl compound of formula (II), of at least one formate ester of formula (III) and/or of at least one alcohol of formula (IV) as defined in claim 1, on a surface or the air surrounding the perfuming composition, wherein the surface, or the air is treated with at least one compound (I) as defined in claim 1, or with a composition or article containing at least one compound (I), under conditions susceptible of allowing the release of at least one ketone formula (II), of at least one formate ester of formula (III) and/or of at least one alcohol of formula (IV) over time.

11. A perfuming composition comprising
i) at least one compound of formula (I), as defined in claim 1;
ii) at least one ingredient selected from the group consisting of a perfumery carrier and a perfumery base; and
iii) optionally at least one perfumery adjuvant.

12. A perfumed consumer product comprising at least one compound of formula (I), as defined in claim 8.

13. The perfumed consumer product according to claim 12, wherein the perfumery consumer product is a perfume, a fabric care product, a body-care product, a cosmetic preparation, a skin-care product, an air care product or a home care product.

14. The perfumed consumer product according to claim 13, wherein the perfumery consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a hair conditioning product, a vanishing cream, a deodorant or antiperspirant, a hair remover, a tanning or sun product, a nail product, a skin cleansing, a makeup, a perfumed soap, a shower or bath mousse, an oil or gel, or a foot/hand care product, a hygiene product, an air freshener, a "ready to use" powdered air freshener, a mold remover, a furniture care product, a wipe, a dish detergent or hard-surface detergent, a leather care product, a car care product.

15. A compound of formula

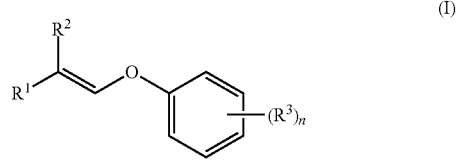

in the form of any one of its stereoisomers or a mixture thereof and wherein when $R^2$ represents a $OR^{2'}$ wherein $R^{2'}$ represents a $C_{1-12}$ alkyl group, a $C_{3-12}$ alkenyl group, phenethyl group, or a benzyl group, then $R^1$ is a phenyl group optionally substituted by one or two RT group wherein $R^{1'}$, simultaneously or independently, represents a hydroxyl group, a $C_{1-3}$ alkyl group, a $C_{1-3}$ alkoxy group or a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring;

when $R^2$ represents a $C_{1-3}$ alkyl, then $R^1$ represents a $C_{1-15}$ alkyl, $C_{2-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a $C_{1-15}$ alkyl, $C_{1-15}$ alkoxy, $C_{3-15}$ cycloalkyl, $C_{5-15}$ cycloalkenyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

n represents an integer between 1 and 3;

$R^3$, simultaneously or independently, represents at least one substituent of the aromatic ring and is a $C_{1-6}$ alkyl group optionally substituted by a hydroxy, $C_{1-6}$ alkoxy, or oxo group; a $C_{2-6}$ alkenyl group; a $C_{1-6}$ alkoxy group; or a $R^bOCO$ group wherein $R^b$ is a hydrogen atom, a $C_{1-7}$ alkyl group, a $C_{2-7}$ alkenyl group, a $C_{3-7}$ cycloalkyl group, a benzyl group or a phenethyl group;

provided that when $R^1$ is methyl then $R^2$ is not methyl, when $R^1$ is ethyl then $R^2$ is not ethyl, 1,3-dimethoxy-2-((2-phenylprop-1-en-1-yl)oxy)benzene, 1-methyl-4-((-2-methyl-4-(2,6,6-trimethylcyclohex-1-en-1-yl) buta-1,3-dien-1-yl)oxy)benzene, 1-methyl-4-((-2-methyl-4-(2,6,6-trimethylcyclohex-2-en-1-yl) buta-1,3-dien-1-yl)oxy)benzene and 1,2-dimethoxy-4-(1-(2-methoxyphenoxy) prop-1-en-2-yl)benzene are excluded.

\* \* \* \* \*

UNITED STATES PATENT AND TRADEMARK OFFICE
CERTIFICATE OF CORRECTION

| | | |
|---|---|---|
| PATENT NO. | : 12,252,465 B2 | Page 1 of 1 |
| APPLICATION NO. | : 17/754486 | |
| DATED | : March 18, 2025 | |
| INVENTOR(S) | : Womack et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Thirtieth Day of September, 2025

John A. Squires
*Director of the United States Patent and Trademark Office*